(12) United States Patent
Barnikow et al.

(10) Patent No.: US 7,888,090 B2
(45) Date of Patent: Feb. 15, 2011

(54) MUTANTS OF $O^6$-ALKYLGUANINE-DNA ALKYLTRANSFERASE

(75) Inventors: Jan Barnikow, Basel (CH);
Christopher Chidley, Crissier (CH);
Thomas Gronemeyer, Hattingen (DE);
Christian Heinis, Aarberg (CH);
Hughes Jaccard, Yverdon-les-Bains (CH); Kai Johnsson, Lausanne (CH);
Alexandre Juillerat, Paris (FR); Antje Keppler, Heidelberg (DE)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 508 days.

(21) Appl. No.: 10/591,159

(22) PCT Filed: Mar. 1, 2005

(86) PCT No.: PCT/EP2005/050899
§ 371 (c)(1),
(2), (4) Date: Oct. 3, 2006

(87) PCT Pub. No.: WO2005/085431
PCT Pub. Date: Sep. 15, 2005

(65) Prior Publication Data
US 2007/0207532 A1    Sep. 6, 2007

(30) Foreign Application Priority Data

Mar. 2, 2004  (EP) ................... 04405123
Jul. 22, 2004  (EP) ................... 04405465

(51) Int. Cl.
*C12N 9/10*  (2006.01)
*C12N 15/00*  (2006.01)
*C12P 21/04*  (2006.01)
*C07H 21/04*  (2006.01)

(52) U.S. Cl. ............ 435/193; 435/440; 435/69.1; 435/71.1; 536/23.2

(58) Field of Classification Search ............ None
See application file for complete search history.

(56) References Cited

FOREIGN PATENT DOCUMENTS

| WO | 98/13487 | 4/1998 |
|---|---|---|
| WO | 02/083937 | 10/2002 |
| WO | 2004/031404 | 4/2004 |
| WO | 2004/031405 | 4/2004 |

OTHER PUBLICATIONS

Mijal et al. The repair of the tobacco specific nitrosamine derived adduct O6-[4-Oxo-4-(3-pyridyl)butyl]guanine by O6-alkylguanine-DNA alkyltransferase variants. Chem Res Toxicol. Mar. 2004;17(3):424-34. publshed on-line on Feb. 12, 2004.*
S. Gendreizig et al., "Induced Protein Dimerization in Vivo through Covalent Labeling", Journal of the American Chemical Society, , vol. 125, No. 49, pp. 14970-14971, Aug. 12, 2003.
A. Juillerat et al., "Directed Evolution of $O^6$-Alkylguanine-DNA Alkyltransferase for Efficient Labeling of Fusion Proteins with Small Molecules In Vivo", Chemistry and Biology, vol. 10, No. 4, pp. 313-317, Apr. 4, 2003.
W. P.C. Stemmer et al., "Rapid Evolution of a Protein In Vitro by DNA Shuffling", Nature, vol. 370, pp. 389-391, Aug. 4, 1994.
M. Xu-Welliver et al., "Point Mutations at Multiple Sites Including Highly Conserved Amino Acids Maintain Activity, but Render O-Benzylguanine", Biochemical Journal, vol. 347, No. 2, pp. 519-526, Apr. 15, 2000.

* cited by examiner

*Primary Examiner*—Yong D Pak
(74) *Attorney, Agent, or Firm*—Harriet M. Strimpel

(57) ABSTRACT

The invention relates to AGT mutants showing, when compared to the wild type human AGT, two or more advantageous properties selected from (a) reduced DNA interaction; (b) localisation of the expressed protein in eukaryotic cells that is no longer restricted to the nucleus; (c) improved expression yield as soluble protein and improved stability in various hosts; (d) improved stability under oxidising conditions; (e) improved stability within cells after reaction with a substrate; (f) improved stability outside cells before and after reaction with a substrate; (g) improved in vitro solubility; (h) improved reactivity against $O^6$-alkylguanine substrates; (1) reduced reactivity against DNA-based substrates; and (j) reduced reactivity against $N^9$-substituted $O^6$-alkylguanine substrates. Such AGT mutants with the mentioned improved properties are mutants wherein between 1 and 25 amino acids of the wild type human AGT are substituted by other amino acids, and optionally 1 to 5 amino acids out of the continuous chain at one, two or three positions are deleted or added and/or 1 to 4 amino acids at the N-terminus or 1 to 40 amino acids at the C-terminus are deleted. The invention further relates to a method for detecting and/or manipulating a protein of interest wherein the protein of interest is incorporated into a fusion protein with the AGT mutants of the invention. Another object of the invention are AGT fusion proteins comprising such AGT mutants and the protein of interest.

36 Claims, 3 Drawing Sheets

MUTANTS OF O⁶-ALKYLGUANINE-DNA ALKYLTRANSFERASE

This application is a U.S. national stage of International Application No. PCT/EP2005/050899 filed Mar. 1, 2005.

FIELD OF THE INVENTION

The present invention relates to mutants of wild type human $O^6$-alkylguanine-DNA alkyltransferase (hAGT) and to methods of transferring a label from substrates to fusion proteins consisting of these $O^6$-alkylguanine-DNA alkyltransferase mutants and proteins of interest.

BACKGROUND OF THE INVENTION

The mutagenic and carcinogenic effects of electrophiles such as N-methyl-N-nitrosourea are mainly due to the $O^6$-alkylation of guanine in DNA. To protect themselves against DNA-alkylation, mammals and bacteria possess a protein, $O^6$-alkylguanine-DNA alkyltransferase (AGT) which repairs these lesions. AGT transfers the alkyl group from the position O-6 of alkylated guanine and guanine derivatives to the mercapto group of one of its own cysteines, resulting in an irreversibly alkylated AGT. The underlying mechanism is a nucleophilic reaction of the $S_N 2$ type which explains why not only methyl groups, but also benzylic groups are easily transferred. As overexpression of human AGT (hAGT, SEQ ID NO:1) in tumour cells is the main reason for resistance to alkylating drugs such as procarbazine, dacarbazine, temozolomide and bis-2-chloroethyl-N-nitrosourea, inhibitors of AGT have been proposed for use as sensitisers in chemotherapy (Pegg et al., Prog Nucleic Acid Res Mol Biol 51:167-223, 1995). U.S. Pat. No. 5,691,307 describes $O^6$-benzylguanines carrying various substituents in the benzyl group, and their use for depleting AGT levels in tumor cells and thereby increasing responsiveness to alkylating anti-tumor drugs. Likewise, WO 97/20843 discloses further AGT depleting compounds representing $O^6$-benzyl- and $O^6$-heteroarylmethyl-pyrimidine derivatives.

DE 199 03 895 discloses an assay for measuring levels of AGT which relies on the reaction between biotinylated $O^6$-alkylguanine derivatives and human AGT which leads to biotinylation of the AGT. This in turn allows the separation of the AGT on a streptavidin coated plate and its detection, e.g. in an ELISA assay. The assay is suggested for monitoring the level of AGT in tumour tissue and for use in screening for AGT inhibitors.

Damoiseaux et al., ChemBiochem 4:285-287, 2001, disclose modified $O^6$-alkylated guanine derivatives incorporated into oligodeoxyribonucleotides for use as chemical probes for labelling human AGT, again to facilitate detecting the levels of this enzyme in cancer cells to aid in research and in chemotherapy.

WO 02/083937 discloses a method for detecting and/or manipulating a protein of interest wherein the protein is fused to AGT and the AGT fusion protein contacted with an AGT substrate carrying a label, and the AGT fusion protein detected and optionally further manipulated using the label. Several AGT fusion proteins to be used, general structural principles of the AGT substrate and a broad variety of labels and methods to detect the label useful in the method are described. Although other forms of AGT are mentioned, only human AGT is exemplified.

PCT/EP03/10859 (WO 2004/031404) describes particular AGT fusion proteins to be used in the mentioned method for detecting and/or manipulating a protein of interest, labelled fusion proteins obtainable by this method, and the method using the particular AGT fusion proteins.

PCT/EP03/10889 (WO 2004/031405) discloses additional AGT substrates carrying a label particularly suitable in the mentioned method for detecting and/or manipulating a protein of interest, and the application of such particularly labelled substrates. This patent application also describes methods of manufacture of these additional AGT substrates.

Human AGT mutant Gly160Trp (Xu-Welliver et al., Biochemical Pharmacology 58:1279-1285, 1999) is somewhat more reactive towards benzylguanine derivatives than wild type human AGT. Juillerat et al., Chem Biol 10:313-317, 2003, prepared a number of mutants of human AGT in the search for more reactive partners for efficient in vivo (intracellular) labeling of AGT fusion proteins with synthetic substrates. Mutations in position 140, 157, 159 and 160 were reported. The mutant Asn157Gly Ser159Glu shows increased activity against benzylguanine derivatives by a factor of approximately 20 compared to wild type hAGT.

The following additional mutations in hAGT have been shown to disrupt DNA binding of hAGT but do not significantly interfere with the activity against benzylguanine derivatives: Lys125Ala, Ala127Thr and Arg128Ala, see Lim et al., EMBO J 15:4050-4060, 1996, and Daniels et al., EMBO J 19:1719-1730, 2000.

The crystal structure of human AGT (pdb-ID 1EH6; Daniels et al., EMBO J 19:1719, 2000) was resolved using a functional protein that was truncated after Asn207.

SUMMARY OF THE INVENTION

The invention relates to AGT mutants showing, when compared to the wild type human AGT, two or more advantageous properties selected from
(a) reduced DNA interaction;
(b) localisation of the expressed protein in eukaryotic cells that is no longer restricted to the nucleus;
(c) improved expression yield as soluble protein and improved stability in various hosts;
(d) improved stability under oxidising conditions;
(e) improved stability within cells after reaction with a substrate;
(f) improved stability outside cells before and after reaction with a substrate;
(g) improved in vitro solubility;
(h) improved reactivity against $O^6$-alkylguanine substrates;
(i) reduced reactivity against DNA-based substrates; and
(j) reduced reactivity against $N^9$-substituted $O^6$-alkylguanine substrates.

AGT mutants of the invention are mutants with the mentioned improved properties wherein between 1 and 25 amino acids of the wild type human AGT are substituted by other amino acids, and optionally 1 to 5 amino acids out of the continuous chain at one, two or three positions are deleted or added and/or 1 to 4 amino acids at the N-terminus or 1 to 40 amino acids at the C-terminus are deleted.

The invention further relates to a method for detecting and/or manipulating a protein of interest wherein the protein of interest is incorporated into a fusion protein with the AGT mutants of the invention. Another object of the invention are AGT fusion proteins comprising such AGT mutants and the protein of interest.

Figure 1:
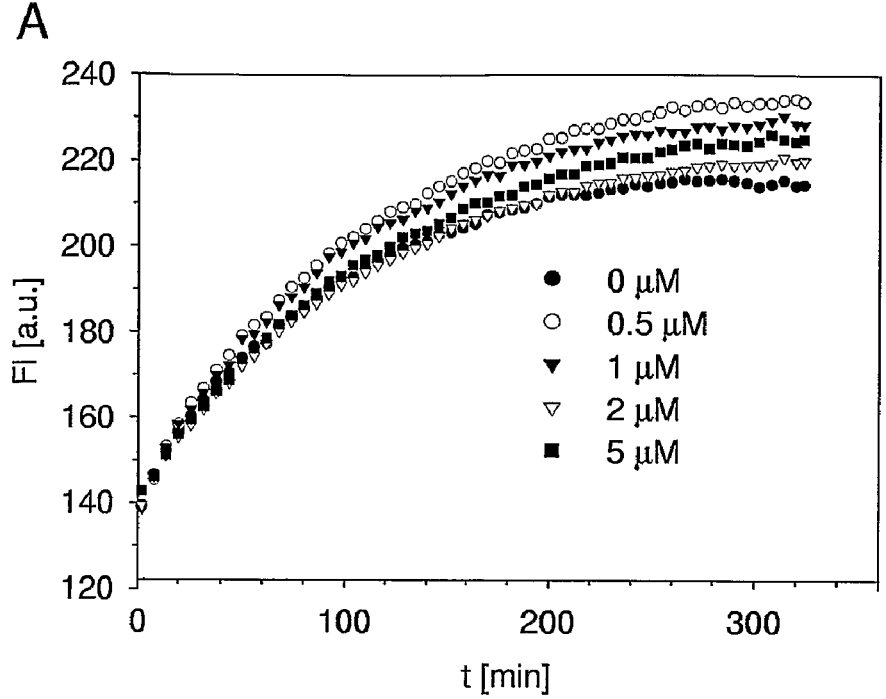
FIG. 1: Reaction of AGTM (mutant of Example 6, A) or PGEG-hAGT (B) with BG-Cy3 in presence of BG-modified oligonucleotide (SEQ ID No:2) at the concentrations shown. The fluorescence FL (excitation 519 nm, emission at 572 nm) in arbitrary units [a.u.], detected on a Spectra Max Gemini plate reader (Molecular Devices), is plotted against time (t) in minutes [min].
Figure 1:
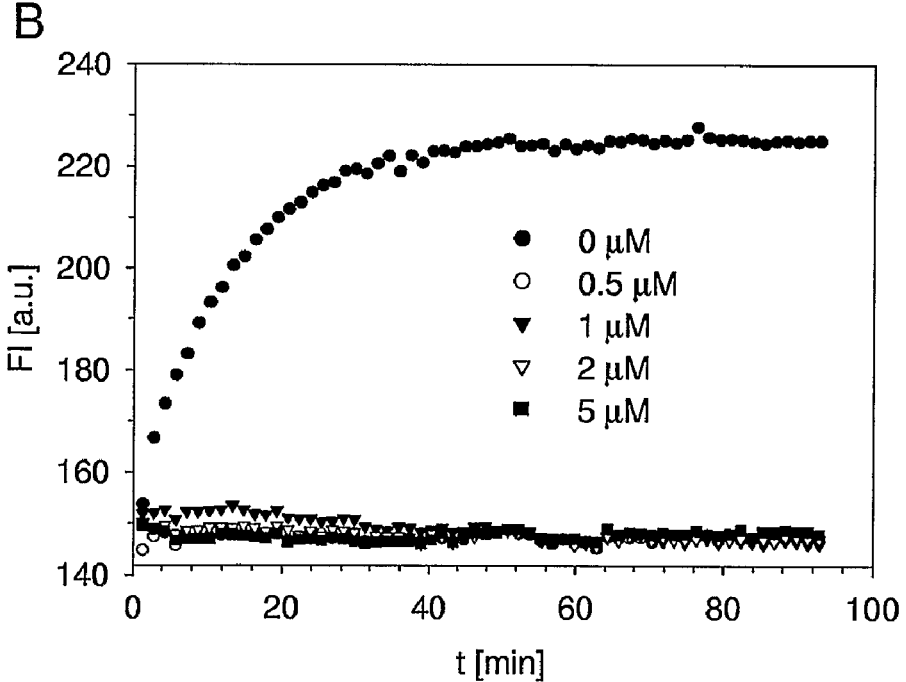
Figure 2:
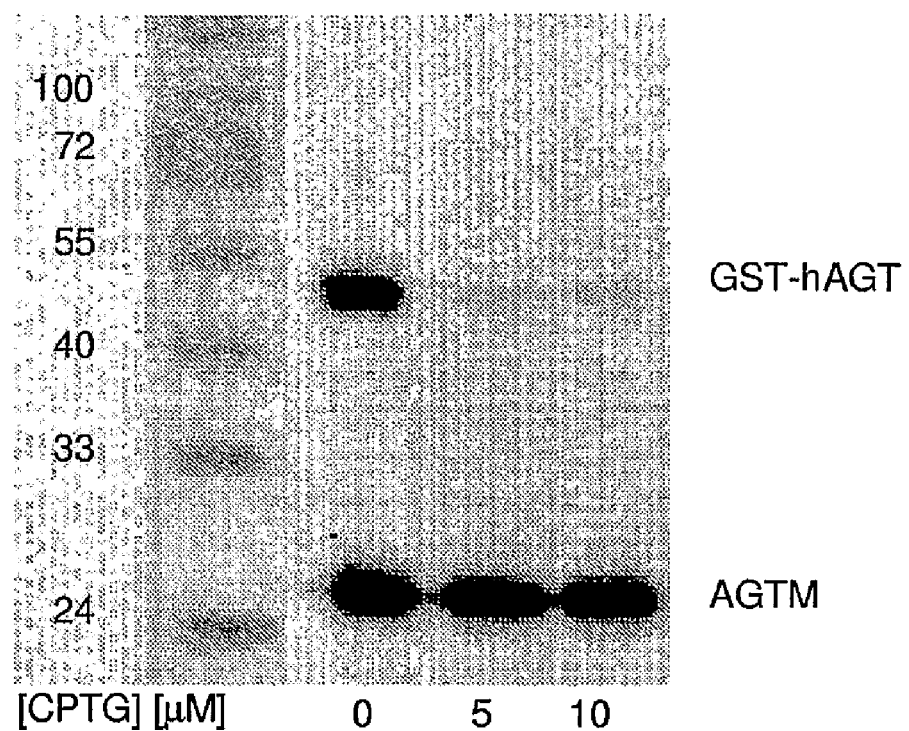
FIG. 2: Western blot of the reaction of wild type hAGT (GST-hAGT fusion protein) and AGTM with the two substrates $N^9$-cyclopentyl-$O^6$-bromophenyl-guanine (CPTG) and biotinylated $O^6$-benzylguanine (BG-Bt, substance 3a of Juillerat et al. 2003) as described in Example 7. BG-Bt is present in all samples at 5 µM. Detection with neutravidin-peroxidase conjugate and luminescent peroxidase substrate detecting any AGT reacted with BG-Bt. Even under simultaneous incubation with identical concentrations of CPTG and BG-Bt only about 5% of GST-hAGT reacts with substrate BG-Bt.

1 Fluorescence of BG-Cy3 without protein; background fluorescence.
2 Reaction with BG-Cy3; no preblocking, positive control.
3 Reaction with BG-Cy3, preblocked with 100 □M BG.
4 Reaction with BG-Cy3, preblocked with 100 □M $N^9$-isobutyl-$O^6$-benzylguanine.
5 Reaction with BG-Cy3, preblocked with 100 □M $N^9$-propyl-$O^6$-benzylguanine.
6 Reaction with BG-Cy3, preblocked with 100 □M $N^9$-cyanomethyl-$O^6$-benzylguanine.

DETAILED DESCRIPTION OF THE INVENTION

In the previously described method for detecting and/or manipulating a protein of interest, wherein the protein of interest is incorporated into an AGT fusion protein, the AGT fusion protein is contacted with particular AGT substrates carrying a label, and the AGT fusion protein is detected and optionally further manipulated using the label in a system designed for recognising and/or handling the label, the performance of AGT can be further improved by replacing the wild type human AGT by mutant AGT. Such an improved method involving mutant AGT is the object of the invention. Another object are AGT mutants particularly suitable for the described method, and AGT fusion proteins comprising such AGT mutants and one or more other proteins including at least one protein of interest. Protein of interest can be any protein.

AGT mutants of the invention comprise e.g. mutants which, when compared to the wild type human AGT or to known AGT mutants, show two or more properties selected from
(a) reduced DNA interaction;
(b) localisation of the expressed protein in eukaryotic cells that is no longer restricted to the nucleus;
(c) improved expression yield as soluble protein and improved stability in various hosts;
(d) improved stability under oxidising conditions;
(e) improved stability within cells after reaction with a substrate;
(f) improved stability outside cells before and after reaction with a substrate;
(g) improved in vitro solubility;
(h) improved reactivity against $O^6$-alkylguanine substrates;
(i) reduced reactivity against DNA-based substrates; and
(j) reduced reactivity against $N^9$-substituted $O^6$-alkylguanine substrates.

(a) Reduced DNA Interaction

A mutant AGT of the invention with "reduced DNA interaction" shows less than 20% of DNA binding, preferably less than 2% of DNA binding, most preferably no detectable DNA binding, when compared to wild type human AGT or to known AGT mutants such as "PGEG-hAGT" (Juillerat et al., Chem Biol 10:313-317, 2003). The interaction with DNA is e.g. quantified by assessing the amount of copurified DNA from E. coli extracts under conditions of low salt and absence of DNase. This is compared between parallel purifications of fusion proteins (e.g. fusions to GST) of wild type (human) and mutant AGT by spectroscopic methods (ratio of absorbance at 260 and 280 nm). Alternatively the interaction of AGT with DNA is measured as the inhibition of AGT reactivity with BG-Cy3 ($O^6$-(4-aminomethyl-benzyl)-guanine coupled to Cy3) as substrate in the presence of DNA. This approach takes advantage of a marked increase of fluorescence of the Cy3 fluorophore upon reaction of BG-Cy3 with AGT. The reaction kinetics of AGT with a Cy3-labeled benzylguanine derivative is followed by fluorescence intensity measurements over several hours at various concentrations of salmon sperm DNA. Wild type hAGT was shown to bind to DNA as a tetramer whereas the unbound hAGT protein stays monomeric (Rasimas et al., J Biol Chem 278(10):7973-80, 2003). AGT mutants that are not able to bind to DNA also do not tetramerise.

(b) Localisation of the Expressed Protein in Eukaryotic Cells that is No Longer Restricted to the Nucleus A mutant AGT of the invention with "localisation no longer restricted to the nucleus" shows substantially uniform localisation of mutant AGT throughout the cell upon expression in eukaryotic cells, e.g. in mammalian cells. Subcellular localisation of AGT mutants is investigated by transiently transfecting AGT-deficient HeLa cells or CHO cells with a construct for constitutive expression under the human cytomegalovirus immediate early □ promoter. The cells are stained with cell membrane permeable diacetylfluorescein-modified $O^6$-benzylguanine (substance 4 of Juillerat et al., Chem Biol 10:313-317, 2003) and analysed by confocal laser scanning microscopy. The fluorescence intensities for cytoplasm and nucleus are compared for mutant and wild type AGT. Wild type human AGT shows preferential localisation in the nucleus, and only marginal localisation in the cytoplasm.

(c) Improved Expression Yield as Soluble Protein and Improved Stability in Various Hosts A mutant AGT of the invention with "improved expression yield as soluble protein", i.e. protein found in the soluble fraction after cell lysis and not in inclusion bodies, shows more than threefold expression yield, preferably more than fivefold expression yield, most preferably more than tenfold expression yield as soluble protein, when compared to wild type human AGT. This increased expression yield is at the same time a measure of "stability in the host" used for expression. Expression yield is measured in E. coli or in any other of the standard production cells for genetically modified proteins, e.g. yeast, or preferably insect cells, CHO cells or HeLa cells. For quantifying expression yield, AGT fusion proteins may be chosen such that the fusion partner allows easy purification and quantification. For example, expression yield in *E. coli* is determined by measuring and comparing the yield of soluble and insoluble GST-wild type AGT fusion protein and GST-mutant AGT fusion protein from parallel *E. coli* expression cultures. Samples of the soluble fractions and insoluble fractions (i.e. the inclusion bodies) after cell lysis are subjected to SDS-PAGE, and the band staining intensities of the corresponding AGT fusion proteins are compared. Soluble protein is quantified after purification of the fusion protein from cell extracts by affinity chromatography (e.g. for GST-AGT fusion proteins by glutathione sepharose) by subjecting the purified fractions to a protein concentration assay (Bradford, Anal Biochem 72:248-54, 1976). The expression yield of similar proteins in the soluble fraction (difference in point mutations) can be used as a measure for protein stability in the unpurified as well as the purified state (Ohage et al., J Mol Biol 291:1119-1128, 1999; Wirtz et al., Protein Sci 8: 2245-50, 1999). Therefore, this is taken as a measure of folding stability and aggregation tendency.

(c') From a practical standpoint, improved expression yields as a soluble protein in *E. coli* is particularly important.

(d) Improved Stability Under Oxidising Conditions

A mutant AGT of the invention with "improved stability under oxidising conditions" shows more than twofold yield of active protein, preferably more than fivefold yield of active protein, most preferably more than tenfold yield of active protein when compared to the wild type AGT or to known AGT mutants such as "PGEG-hAGT" (Juillerat et al., Chem Biol 10:313-317, 2003), i.e. the AGT protein retains its activity towards AGT substrates after an incubation time of one or more hours under oxidising conditions in buffered aqueous solution (e.g. 100 mM NaCl, 10 mM HEPES, pH 7.4, no dithiothreitol or beta-mercaptoethanol added). The activities towards AGT substrates are measured after purification without addition of reducing agents such as dithiothreitol or beta-mercaptoethanol. Alternatively, the activities of mutant AGT and wild type human are compared after their export into cellular compartments with oxidising redox potential (e.g. the periplasm of *E. coli* due to their fusion to appropriate signal sequences. Activity towards AGT substrates under reducing and oxidising conditions is compared by performing the reactions in the presence or absence of reducing agents such as dithiothreitol or beta-mercaptoethanol.

(e) Improved Stability within Cells after Reaction with a Substrate

A mutant AGT of the invention with "improved stability within cells" shows, after reaction with a cell permeable substrate inside a cell (e.g. a mammalian cell), more than twofold stability, preferably more than threefold stability, most preferably more than sixfold stability, when compared to wild type human AGT or to known AGT mutants such as "PGEG-hAGT" (Juillerat et al., Chem Biol 10:313-317, 2003). Stability is determined for a mutant AGT fusion protein after reaction with an AGT substrate by analysing the intensity and the localisation of AGT fusion proteins with confocal laser scanning microscopy.

(f) Improved Stability Outside Cells Before and after Reaction with a Substrate

A mutant AGT of the invention with "improved stability outside cells" shows more than twofold stability, preferably more than fourfold stability, most preferably more than sixfold stability, when compared to wild type human AGT or to known AGT mutants such as "PGEG-hAGT" (Juillerat et al., Chem Biol 10:313-317, 2003). Stability before reaction is determined for the mutant AGT or for a mutant AGT fusion protein by incubating purified samples in buffered aqueous solution for up to two weeks at 4° C. and up to six months at −20° C. At several time points, aliquots are taken and concentration of reactive AGT is estimated as described by Juillerat et al., Chem Biol 10:313-317, 2003. Stability for wild type AGT and the AGT mutant after reaction with a labelled substrate and after subsequent separation from unreacted substrate is determined by quantifying the concentration of the label in the soluble fraction over up to two weeks at 4° C. and up to three months at −20° C.

(f') From a practical standpoint, stability after reaction with a labelled substrate is particularly important.

(g) Improved in Vitro Solubility

A mutant AGT of the invention with "improved in vitro solubility" shows more than twofold solubility, preferably more than fivefold solubility, most preferably more than tenfold solubility, when compared to wild type human AGT. The in vitro solubility of wild type AGT and the AGT mutant is measured by determining the amount of protein that remains in the soluble fraction after overnight incubation of purified samples at 4° C. or up to 37° C. at one or several concentrations established in a suitable buffer (e.g. 100 mM NaCl, 20 mM Tris, pH 8.0, 20% glycerol, 1 mM DTT).

(h) Improved Reactivity Against $O^6$-Alkylguanine Substrates

A mutant AGT of the invention with "improved reactivity" shows more than threefold reactivity, preferably more than fivefold reactivity, most preferably more than tenfold reactivity, when compared to wild type human AGT. Activity towards $O^6$-benzylguanine substrates is measured as described by Juillerat et al., Chem Biol 10:313-317, 2003.

(i) Reduced Reactivity Against DNA-Based Substrates

A mutant AGT of the invention with "reduced reactivity against DNA-based substrates" shows less than 10% reactivity against DNA-based substrates, preferably less than 1% reactivity against DNA-based substrates, most preferably no detectable reactivity against DNA-based substrates, when compared to wild type human AGT. The ability of wild type AGT or mutant AGT to react with alkylated DNA substrates is measured as the reaction of its inactivation by a synthetic oligonucleotide containing $O^6$-benzylguanine (SEQ ID NO:2, modified in position 14). Subsequently, the reactions are quenched by incubation with biotinylated $O^6$-alkylguanine. Samples are subjected to Western blotting and detection with streptavidin derivates to obtain kinetic constants for these substrates. Alternatively, the ability of wild type or mutant AGT to react with alkylated DNA substrates is measured via its labeling efficiency in competition with a fluorescent substrate of AGT. The reaction kinetics of AGT with BG-Cy3 ($O^6$-benzylguanine coupled to Cy3) is followed by fluorescence intensity measurements at various concentrations of a competing synthetic oligonucleotide containing $O^6$-benzylguanine (SEQ ID NO:2, modified in position 14).

(j) Reduced Reactivity Against $N^9$-Substituted $O^6$-Alkylguanine Substrates

A mutant AGT of the invention with "reduced reactivity against $N^9$-substituted $O^6$-alkylguanine substrates" shows less than 10% reactivity, preferably less than 2% reactivity, most preferably no detectable reactivity against $N^9$-substituted $O^6$-alkylguanine substrates, when compared to wild type human AGT or to known AGT mutants such as "PGEG-hAGT" (Juillerat et al, Chem Biol 10:313-317, 2003). Such $N^9$-substituted $O^6$-alkylguanine substrates are the natural substrates of the wild type AGT. The ability of wild type AGT or mutant AGT to react with $N^9$-modified $O^6$-alkylguanine substrates is measured as the rate of its reaction with such substrates, e.g. with the low molecular weight $N^9$-cyclopentyl-$O^6$-benzylguanine in presence of biotinylated $N^9$-unsubstituted $O^6$-alkylguanine substrates in competition experiments. Subsequently, samples are subjected to Western blotting and detection with streptavidin derivates to obtain kinetic constants for these substrates. Alternatively, the reactivity towards such substrates is measured as the inhibition of the reaction of AGT with BG-Cy3. The reaction of AGT with BG-Cy3 is followed by an increase of Cy3 fluorescence intensity upon binding to AGT, after preincubation or in direct competition with the $N^9$-modified $O^6$-alkylguanine substrate.

Preferred AGT mutants of the invention are those which have several preferred properties in common, e.g. those which show (c) improved expression yield as soluble protein and improved stability in various hosts and
(h) improved reactivity against $O^6$-alkylguanine substrates;

or (c) improved expression yield as soluble protein and improved stability in various hosts,
(d) improved stability under oxidising conditions,
(g) improved in vitro solubility, and
(h) improved reactivity against $O^6$-alkylguanine substrates;

or (c) improved expression yield as soluble protein and improved stability in various hosts,
(d) improved stability under oxidising conditions,
(f) improved stability outside cells before and after reaction with a substrate,
(g) improved in vitro solubility, and
(h) improved reactivity against $O^6$-alkylguanine substrates;

or (a) reduced DNA interaction,
(b) localisation of the expressed protein in eukaryotic cells that is no longer restricted to the nucleus,
(c) improved expression yield as soluble protein and improved stability in various hosts,
(h) improved reactivity against $O^6$-alkylguanine substrates, and
(i) reduced reactivity against DNA-based substrates;

or (a) reduced DNA interaction,
(b) localisation of the expressed protein in eukaryotic cells that is no longer restricted to the nucleus,
(c) improved expression yield as soluble protein and improved stability in various hosts,
(e) improved stability within cells after reaction with a substrate,
(h) improved reactivity against $O^6$-alkylguanine substrates, and
(i) reduced reactivity against DNA-based substrates;

or (a) reduced DNA interaction,
(b) localisation of the expressed protein in eukaryotic cells that is no longer restricted to the nucleus,
(c) improved expression yield as soluble protein and improved stability in various hosts,
(h) improved reactivity against $O^6$-alkylguanine substrates,
(i) reduced reactivity against DNA-based substrates, and
(j) reduced reactivity against $N^9$-substituted $O^6$-alkylguanine substrates;

or (a) reduced DNA interaction,
(b) localisation of the expressed protein in eukaryotic cells that is no longer restricted to the nucleus,
(c) improved expression yield as soluble protein and improved stability in various hosts,
(e) improved stability within cells after reaction with a substrate,
(h) improved reactivity against $O^6$-alkylguanine substrates,
(i) reduced reactivity against DNA-based substrates, and
(j) reduced reactivity against $N^9$-substituted $O^6$-alkylguanine substrates;

More preferred AGT mutants are those which show (c) more than fivefold expression yield as soluble protein and improved stability in various hosts, in particular (c') in *E. coli*, and
(h) improved reactivity against $O^6$-alkylguanine substrates;

or (c) more than fivefold expression yield as soluble protein and improved stability in various hosts, in particular (c') in *E. coli*,
(d) more than fivefold stability under oxidising conditions,
(g) more than fivefold in vitro solubility, and
(h) more than fivefold reactivity against $O^6$-alkylguanine substrates;

or (c) more than fivefold expression yield as soluble protein and improved stability in various hosts, in particular (c') in *E. coli*,
(d) more than fivefold stability under oxidising conditions,
(f) more than fourfold stability outside cells before and, in particular (f'), after reaction with a substrate,
(g) more than fivefold in vitro solubility, and
(h) improved reactivity against $O^6$-alkylguanine substrates;

or (a) less than 2% of DNA binding,
(b) localisation of the expressed protein in eukaryotic cells that is no longer restricted to the nucleus,
(c) more than fivefold expression yield as soluble protein and improved stability in various hosts, in particular (c') in *E. coli*,
(h) more than fivefold reactivity against $O^6$-alkylguanine substrates, and
(i) less than 1% reactivity against DNA-based substrates;

or (a) less than 2% of DNA binding,
(b) localisation of the expressed protein in eukaryotic cells that is no longer restricted to the nucleus,
(c) more than fivefold expression yield as soluble protein and improved stability in various hosts, in particular (c') in *E. coli*,
(e) more than threefold stability within cells after reaction with a substrate,
(h) more than fivefold reactivity against $O^6$-alkylguanine substrates, and
(i) less than 1% reactivity against DNA-based substrates;

or (a) less than 2% of DNA binding,
(b) localisation of the expressed protein in eukaryotic cells that is no longer restricted to the nucleus,
(c) more than fivefold expression yield as soluble protein and improved stability in various hosts, in particular (c') in *E. coli*, (h) more than fivefold reactivity against $O^6$-alkylguanine substrates,
(i) less than 1% reactivity against DNA-based substrates, and
(j) less than 2% reactivity against $N^9$-substituted $O^6$-alkylguanine substrates;

or
(a) less than 2% of DNA binding,
(b) localisation of the expressed protein in eukaryotic cells that is no longer restricted to the nucleus,
(c) more than fivefold expression yield as soluble protein and improved stability in various hosts, in particular (c') in *E. coli*
(e) more than threefold stability within cells after reaction with a substrate,
(h) more than fivefold reactivity against $O^6$-alkylguanine substrates,
(i) less than 1% reactivity against DNA-based substrates, and
(j) less than 2% reactivity against $N^9$-substituted $O^6$-alkylguanine substrates;
Most preferred AGT mutants are those which show
(c) more than tenfold expression yield as soluble protein and improved stability in various hosts, in particular (c') in *E. coli*,
(d) more than tenfold stability under oxidising conditions,
(f) more than sixfold stability outside cells before and, in particular (f'), after reaction with a substrate,
(g) more than tenfold in vitro solubility, and
(h) more than tenfold reactivity against $O^6$-alkylguanine substrates;

or
(a) no detectable DNA binding,
(b) localisation of the expressed protein in eukaryotic cells that is no longer restricted to the nucleus,
(c) more than tenfold expression yield as soluble protein and improved stability in various hosts, in particular (c') in *E. coli*,
(e) more than sixfold stability within cells after reaction with a substrate,
(h) more than tenfold reactivity against $O^6$-alkylguanine substrates, and
(i) no detectable reactivity against DNA-based substrates;

or
(a) no detectable DNA binding,
(b) localisation of the expressed protein in eukaryotic cells that is no longer restricted to the nucleus,
(c) more than tenfold expression yield as soluble protein and improved stability in various hosts, in particular (c') in *E. coli*,
(e) more than sixfold stability within cells after reaction with a substrate,
(h) more than tenfold reactivity against $O^6$-alkylguanine substrates,
(i) no detectable reactivity against DNA-based substrates, and
(j) no detectable reactivity against $N^9$-substituted $O^6$-alkylguanine substrates;

or
(a) reduced DNA interaction,
(b) localisation of the expressed protein in eukaryotic cells that is no longer restricted to the nucleus,
(c) more than tenfold expression yield as soluble protein and improved stability in various hosts, in particular (c') in *E. coli*,
(d) more than tenfold stability under oxidising conditions,
(e) more than sixfold stability within cells after reaction with a substrate,
(f) more than sixfold stability outside cells before and, in particular (f'), after reaction with a substrate,
(g) more than tenfold in vitro solubility,
(h) more than tenfold reactivity against $O^6$-alkylguanine substrates, and
(i) no detectable reactivity against DNA-based substrates;

or
(a) reduced DNA interaction,
(b) localisation of the expressed protein in eukaryotic cells that is no longer restricted to the nucleus,
(c) more than tenfold expression yield as soluble protein and improved stability in various hosts, in particular (c') in *E. coli*,
(d) more than tenfold stability under oxidising conditions,
(e) more than sixfold stability within cells after reaction with a substrate,
(f) more than sixfold stability outside cells before and, in particular (f'), after reaction with a substrate,
(g) more than tenfold in vitro solubility,
(h) more than tenfold reactivity against $O^6$-alkylguanine substrates,
(i) no detectable reactivity against DNA-based substrates, and
(j) no detectable reactivity against $N^9$-substituted $O^6$-alkylguanine substrates.

The AGT mutants of the state of the art only have some of the many desirable properties. For example the mutants described by Lim et al., EMBO J 15:4050-4060, 1996 show reduced DNA binding and localisation in the cytoplasm on expression in mammalian cells. Mutants described by Juillerat et al., Chem Biol 10:313-317, 2003, show increased reactivity towards $O^6$-benzylguanine derivatives.

AGT mutants of the invention are mutants with the mentioned improved properties compared to wild type human AGT, wherein between 1 and 25, preferably between 6 and 22, in particular 7, 8, 9, 10, 11, 12, 13, 14, 15, 16, 17, 18 or 19 amino acids of the wild type human AGT are substituted by other amino acids, and optionally 1 to 5 amino acid out of the continuous chain at one, two or three positions are deleted or added and/or 1 to 4 amino acids at the N-terminus or 1 to 40, preferably 20 to 35, in particular 25 to 30 amino acids at the C-terminus are deleted.

Preferably, amino acids in the following positions are replaced:
(A) Cys62, replaced by Ala or Val, preferably by Ala, which increases the expression yield in *E. coli* and renders the protein less susceptible to oxidation.
(B) Gln 15-Gln116, replaced by Ala-Asn, Asn-Asn, Ser-His, Ser-Ser, Pro-Pro, Pro-Ser, Pro-Thr, or Thr-Ser, preferably by Ser-His, which allows increased expression in *E. coli* and retains substrate reactivity comparable to wild type human AGT, in combination with other amino acid replacements, preferably replacement of Cys150-Ser151-Ser152, in particular replacement of Cys150.
(C) Lys125 replaced by Ala and Ala127-Arg128 replaced by Thr-Ala, which increases expression yield in *E. coli*, reduces DNA binding and abolishes nuclear localisation in mammalian cells (Lim et al., EMBO J 15:4050-4060, 1996), in combination with other amino acid replacements, preferably replacement of Gln115-Gln16/Cys150-Ser151-Ser152 or replacement of Gly131-Gly132/Met134-Arg135, in particular replacement of Cys62/Gln115-Gln116/Gly131-Gly132/Met134-Arg135/Cys150-Ser151-Ser152 and truncation after 182.
(D) Gly131-Gly132/Met134-Arg135 replaced by Val-His/Leu-Arg, Lys-Thr/Leu-Ser, Gln-Val/Leu-Ser, or Met-Thr/Met-Val, preferably Lys-Thr/Leu-Ser, or Gly131-Gly132/

Met134 replaced by Val-His/Leu, which increases expression yield in the periplasm and cytoplasm of *E. coli*, reduces DNA binding and abolishes reactivity with oligonucleotides (containing $O^6$-alkyl-$N^9$-deoxyribosylguanine), $O^6$-alkyl-$N^9$-deoxyribosylguanine and $N^9$-cyclopentyl-$O^6$-benzylguanine or other $N^9$ substituted $O^6$-benzylguanines, while increasing reactivity towards $O^6$-alkylguanine substrates not substituted in the $N^9$ position.

(E) Cys150-Ser151-Ser152 replaced by Asn-Ile-Asn, Pro-Leu-Pro, Pro-Arg-Thr, Ser-Phe-Pro-, or Ser-His-Thr-, preferably by Asn-Ile-Asn, or Cys150-Ser151 replaced by Phe-Asn or Arg-Asn, or Cys 150/Ser152 replaced by His/Thr, Leu/Asn, Leu/Asn, Leu/Pro or Pro/Leu, or Cys 150 replaced by Ser or Thr, which allows more efficient expression in the periplasm of *E. coli* compared to wild type hAGT, retains reactivity towards $O^6$-alkylguanine substrates and renders the protein less sensible to oxidation and decreases DNA-binding.

(F) Pro140/Asn157/Ser159 replaced by Phe/Arg/Glu, or Pro140/Asn157/Gly160 replaced by Met/Trp/Val, or Asn157/Ser159-Gly160 replaced by Gly/Glu-Ala, Gly/Asn-Trp, Pro/Gln-Cys or Gly-Gln-Trp, most preferably Gly-Glu-Ala, or Asn157/Ser159 replaced by Gly/Glu (especially preferred), or Asn157 replaced by Gly or Arg in combination with other amino acid replacements, preferable with replacement of Gln115-Gln116/Cys150-Ser151-Ser152 or replacement of Gly131-Gly132/Met134-Arg135, in particular replacement of Cys62/Gln115-Gln116/Lys125/Ala127-Arg128/Gly131-Gly132/Met134-Arg135/Cys150-Ser151-Ser152 and truncation after 182, which increases the reaction rate towards $O^6$-benzylguanine substrates not substituted in the $N^9$ position (Juillerat et al., Chem Biol 10:313-317, 2003) while increasing the expression yield in the periplasm and cytoplasm of *E. coli*, reducing DNA binding and abolishing reactivity with oligonucleotides (containing $O^6$-alkyl-$N^9$-deoxyribosylguanine), $O^6$-alkyl-$N^9$-deoxyribosylguanine and $N^9$-cyclopentyl-$O^6$-benzylguanine.

(G) Truncation after Gly182 (amino acids 183-207 deleted), which increases expression yield slightly.

Mutants of the invention are especially those wherein two out of the modifications (A), (B), (D), (E), (F) and (G) are present, and optionally 1 to 10, in particular 3 to 7 additional amino acid modifications, and those wherein three or more, for example three or four out of the modifications (A) to (G) are present, and optionally 1 to 10, in particular 3 to 7 additional amino acid modifications. Other preferred mutants are those wherein three or more, for example three or four out of the modifications (A), (B), (C), (E), (F) and (G) are present, and optionally 1 to 10, in particular 3 to 7 additional amino acid modifications.

Particularly preferred are mutant Cys62Ala, Lys125Ala, Ala127Thr, Arg128Ala, Asn157Gly, Ser159Glu, truncated after Gly182, which shows increased expression yield in *E. coli*, reduced sensitivity to oxidation, distribution throughout the cytoplasm in CHO cells, reduced DNA binding, and increased reactivity towards $O^6$-benzylguanine substrates, mutant Gly131Lys, Gly132Thr, Met134Leu, Arg135Ser, Asn157Gly, Ser159Glu, which shows increased expression yield in *E. coli*, at least 1000 fold reduced DNA binding, increased reactivity towards $O^6$-benzylguanine substrates, and substantially reduced reactivity towards $O^6$-alkyl-$N^9$-deoxyribosylguanine or $N^9$-cyclopentyl-$O^6$-benzylguanine, mutant Gln115Ser, Gln116His, Cys150Asn, Ser151Ile, Ser152Asn, Asn157Gly, Ser159Glu, which shows substantially increased expression yield in *E. coli*, but retains activity towards $O^6$-benzylguanine substrates, mutant Cys62Ala, Gln115Ser, Gln116His, Lys125Ala, Ala127Thr, Arg128Ala, Gly131Lys, Gly132Thr, Met134Leu, Arg135Ser, Cys150Asn, Ser151Ile, Ser152Asn, Asn157Gly, Ser159Glu, truncated after Gly182, which shows increased expression yield in *E. coli*, reduced sensitivity to oxidation, distribution throughout the cytoplasm in CHO cells, at least 1000 fold reduced DNA binding, increased reactivity towards $O^6$-benzylguanine substrates, and at least 100 fold reduced reactivity towards $O^6$-alkyl-$N^9$-deoxyribosylguanine or $N^9$-cyclopentyl-$O^6$-benzylguanine, and mutant Cys62Ala, Gln115Ser, Gln116His, Lys125Ala, Ala127Thr, Arg128Ala, Cys150Asn, Ser151Ile, Ser152Asn, Asn157Gly, Ser159Glu, truncated after Gly182, which shows increased expression yield in *E. coli*, reduced sensitivity to oxidation, distribution throughout the cytoplasm in CHO cells, at least 1000 fold reduced DNA binding, and increased reactivity towards $O^6$-benzylguanine substrates, but retain reactivity towards $O^6$-alkyl-$N^9$-deoxyribosyl-guanine or $N^9$-cyclopentyl-$O^6$-benzylguanine.

Further mutants considered are the AGT mutant with modifications Cys62Ala, Lys125Ala, Ala127Thr, Arg128Ala, Gly131Lys, Gly132Thr, Met134Leu, Arg135Ser, Cys150Ser, Asn157Gly, Ser159Glu, truncated after Gly182, and optionally 1 to 15, preferably 1 to 10, in particular 3 to 7 additional amino acid modifications, for example further mutations selected from Gln115Ser, Gln116His;
Ser150Asn, Ser151Ile, Ser152Asn;
Lys8Thr, Lys32Ile, Leu33Phe, Thr127Ala, Ser150Asp, Ser151Gly, Ala154Thr;
Lys32Ile, Leu33Phe, Ser150Val, Ser152Arg, Gly153Asp, Ala154Asp;
Lys32Ile, Leu33Phe, Ser150Gly, Ser151Gly, Ser152Asp, Ala154Asp;
Ser150Val, Ala154Asp;
Ser150Glu, Ser151Gly, Ser152Glu, Ala154Arg;
Lys8Thr, Thr127Ala, Ala154Thr;
Lys32Ile, Leu33Phe;
Ala154Thr;
Leu33Phe;
Ser151Gly;
Ser150Asp;
Thr127Ala; and
Lys32Ile, Leu33Phe, and deletion of Leu34

Mutants considered likewise are the AGT mutant with modifications Cys62Ala, Gln115Ser, Gln116His, Lys125Ala, Ala127Thr, Arg128Ala, Cys150Asn, Ser151Ile, Ser152Asn, Asn157Gly, Ser159Glu, truncated after Gly182 and optionally 1 to 10, in particular 3 to 7 additional amino acid modifications, for example further mutations selected from Lys8Thr, Lys32Ile, Leu33Phe, Thr127Ala, Asn150Asp, Ile151Gly, Ala154Thr;
Lys32Ile, Leu33Phe, Asn150Val, Ile151Ser, Asn152Arg, Gly153Asp, Ala154Asp;
Lys32Ile, Leu33Phe, Asn150Gly, Ile151Gly, Asn152Asp, Ala154Asp;
Asn150Val, Ala154Asp;
Asn150Glu, Ile151Gly, Asn152Glu, Ala154Arg;
Lys8Thr, Thr127Ala, Ala 154Thr;
Lys32Ile, Leu33Phe;

Ala154Thr;
Leu33Phe;
Ile151Gly;
Asn150Asp;
Thr127Ala; and
Lys32Ile, Leu33Phe, and deletion of Leu34.

Likewise preferred is the AGT mutant with modifications Cys62Ala, Lys125Ala, Ala127Thr, Arg128Ala, Cys150Ser, Asn157Gly, Ser159Glu, truncated after Gly182; and the AGT mutant with modifications Cys62Ala, Lys125Ala, Ala127Thr, Arg128Ala, Gly131Lys, Gly132Thr, Met134Leu, Arg135Ser, Cys150Ser, Asn157Gly, Ser159Glu, truncated after Gly182.

Particularly preferred are the compounds of the Examples, in particular of Examples 2 to 7 and Table 1.

Mutants are obtained by techniques well known to those skilled in the art. AGT variants may preferably be produced using protein engineering techniques known to the skilled person and/or using molecular evolution to generate and select new $O^6$-alkylguanine-DNA alkyltransferases. Such techniques are e.g. site directed mutagenesis, saturation mutagenesis, error prone PCR to introduce variations anywhere in the sequence, and DNA shuffling used after saturation mutagenesis. With the aid of the phage display method mutants are found with significantly increased activity towards $O^6$-benzylguanine and AGT substrates of the invention and with increased stability under oxidising conditions. AGT can be functionally displayed as a fusion protein with the phage capsid protein pIII on filamentous phage, and the unusual mechanism of AGT can be used to select phages displaying AGT with improved properties, e.g. increased reaction rate, see Juillerat et al., Chem Biol 10:313-317, 2003.

In the present invention the protein or peptide of interest is fused to the AGT mutant described above. The protein or peptide of interest may be of any length and both with and without secondary, tertiary or quaternary structure, and preferably consists of at least twelve amino acids and up to 2000 amino acids. Examples of such protein or peptide of interest are provided below, and are e.g. enzymes, DNA-binding proteins, transcription regulating proteins, membrane proteins, nuclear receptor proteins, nuclear localization signal proteins, protein cofactors, small monomeric GTPases, ATP-binding cassette proteins, intracellular structural proteins, proteins with sequences responsible for targeting proteins to particular cellular compartments, proteins generally used as labels or affinity tags, and domains or subdomains of the aforementioned proteins. The protein or peptide of interest is preferably fused to the AGT mutant by way of a linker which may be cleaved by an enzyme, e.g. at the DNA stage by suitable restriction enzymes, e.g. AGATCT cleavable by Bgl II, and/or linkers cleavable by suitable enzymes at the protein stage, e.g. tobacco etch virus NIa (TEV) protease. Fusion proteins may be expressed in prokaryotic hosts, preferably *E. coli*, or eukaryotic hosts, e.g. yeast, insect or mammalian cells.

The AGT mutant has the property of transferring a label present on a suitable substrate described below to one of the cysteine residues of the AGT part of a fusion protein.

The fusion protein comprising protein of interest and the AGT mutant is contacted with a particular substrate having a label, as described below. Conditions of reaction are selected such that the AGT mutant reacts with the substrate and transfers the label of the substrate. Usual conditions are a buffer solution at around pH 7 at room temperature, e.g. around 25° C. However, it is understood that the AGT mutant reacts also under a variety of other conditions, and those conditions mentioned here are not limiting the scope of the invention.

The label part of the substrate can be chosen by those skilled in the art dependent on the application for which the fusion protein is intended. After contacting the fusion protein comprising AGT mutant with the substrate, the label is covalently bonded to the fusion protein. The labelled AGT mutant fusion protein is then further manipulated and/or detected by virtue of the transferred label. The label may consist of a plurality of same or different labels. If the substrate contains more than one label, the corresponding labelled AGT mutant fusion protein will also comprise more than one label which gives more options for further manipulating and/or detecting the labelled fusion protein.

Under "manipulation" any physical or chemical treatment is understood. For instance manipulation may mean isolation from cells, purification with standard purification techniques, e.g. chromatography, reaction with chemical reagents or with the binding partner of a binding pair, in particular if the binding partner is fixed to a solid phase, and the like. Such manipulation may be dependent on the label L, and may occur in addition to "detection" of the labelled fusion protein. If the labelled fusion protein is both manipulated and detected, detection may be before or after manipulation, or may occur during manipulation as defined herein.

The particular AGT substrates are those disclosed in patent application PCT/EP03/10889 (WO 2004/031405), e.g. compounds of formula (I)

wherein $R_1$—$R_2$ is a group recognized by AGT as a substrate;
X is oxygen or sulfur;
$R_3$ is an aromatic or a heteroaromatic group, or an optionally substituted unsaturated alkyl, cycloalkyl or heterocyclyl group with the double bond connected to $CH_2$;
$R_4$ is a linker; and
L is a label, a plurality of same or different labels, a bond connecting $R_4$ to $R_1$ forming a cyclic substrate, or a further group —$R_3$—$CH_2$—X—$R_1$—$R_2$.

In a group $R_1$—$R_2$, the residue $R_1$ is preferably a heteroaromatic group containing 1 to 5 nitrogen atoms, recognized by AGT as a substrate, preferably a purine radical of the formula (II)

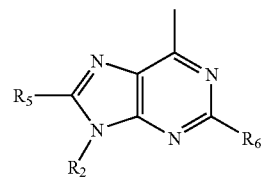

wherein $R_2$ is hydrogen, alkyl of 1 to 10 carbon atoms, or a saccharide moiety;
$R_5$ is hydrogen, halogen, e.g. chloro or bromo, trifluoromethyl, or hydroxy; and
$R_6$ is hydrogen, hydroxy or unsubstituted or substituted amino.

If $R_5$ or $R_6$ is hydroxy, the purine radical is predominantly present in its tautomeric form wherein a nitrogen adjacent to the carbon atom bearing $R_5$ or $R_6$ carries a hydrogen atom, the double bond between this nitrogen atom and the carbon atom bearing $R_5$ or $R_6$ is a single bond, and $R_5$ or $R_6$ is double bonded oxygen, respectively.

If $R_6$ is unsubstituted or substituted amino and the residue X connected to the bond of the purine radical is oxygen, the residue of formula (II) is a guanine derivative.

Other particular substrates useful in the method of the invention are compounds of formula (I) wherein $R_1$ is a purine radical of formula (II) and $R_2$ is cycloalkyl, e.g. cyclopentyl, or alkyl, e.g. propyl or isobutyl, or substituted alkyl, e.g. cyanomethyl.

The present invention provides a method to label AGT mutant fusion proteins both in vivo (intracellular) as well as in vitro. The term in vivo labelling of a AGT mutant fusion protein includes labelling in all compartments of a cell as well as of AGT mutant fusion proteins pointing to the extracellular space. If the labelling of the AGT mutant fusion protein is done in vivo and the protein fused to the AGT mutant is a membrane protein, more specifically a plasma membrane protein, the AGT part of the fusion protein can be attached to either side of the membrane, e.g. attached to the cytoplasmic or the extracellular side of the plasma membrane.

If the labelling is done in vitro, the labelling of the fusion protein can be either performed in cell extracts or with purified or enriched forms of the AGT mutant fusion protein.

If the labelling is done in vivo (intracellular) or in cell extracts, the labelling of the endogenous AGT of the host can be advantageously taken into account. If the endogenous AGT of the host does not accept $O^6$-alkylguanine derivatives or related compounds as a substrate, the labelling of the fusion protein is specific. In mammalian cells, e.g. in human, murine, or rat cells, labelling of endogenous AGT is possible. In those experiments where the simultaneous labelling of the endogenous AGT as well as of the AGT mutant fusion protein poses a problem, known AGT-deficient cell lines can be used.

When using a mutant AGT fusion protein that is non-reactive against a particular substrate in turn recognized by the endogenous AGT, such a non-reactive substrate can be used for blocking the activity of endogenous AGT before or while incubating the cells with a substrate designed to react with the particular mutant AGT fusion protein. For example, a mutant AGT may be used that does not react with $N^9$-substituted $O^6$-alkylguanine derivatives, e.g. with $N^9$-cyclopentyl-$O^6$-benzylguanine. In mammalian cells containing endogenous AGT, this wild type AGT can then be blocked with $N^9$-cyclopentyl-$O^6$-benzylguanine prior to labeling or while labeling a mutant AGT fusion protein with a different substrate recognized by this mutant AGT.

If no significant levels of endogenous wild type AGT are present in a particular biological sample, there will be no need for pre-inactivating the endogenous AGT using a substrate for which the mutant AGT selected for the experiment is not reactive. Under such conditions the availability of a mutant AGT fusion protein which does not react with a particular substrate of the wild type AGT allows to label selectively two different mutants of AGT (or one mutant of AGT and wild type hAGT) with two different substrates. This is achieved by using a mutant AGT, here designated "AGT-A", which shows a selectivity for low molecular weight substrates comparable to the wild type hAGT protein, and another mutant AGT designated "AGT-B" which reacts tenfold or preferably hundredfold less rapid with a particular substrate of the wild type hAGT. Having both mutant "AGT-A" (or wild type AGT) and mutant "AGT-B" present in a biological sample, reacting that biological sample—e.g. a cell extract or intact cells—first for a limited time with the substrate which is selectively recognized by mutant "AGT-A" (or wild type AGT), leading to complete or almost complete turnover of the mutant "AGT-A" protein (or wild type AGT) with substrate "A", but leaving the mutant "AGT-B" protein unreacted or almost unreacted, followed by an incubation with substrate "B" for which mutant "AGT-B" is reactive (and mutant "AGT-A" or wild type AGT may also be reactive), leading to a preferential reaction of mutant "AGT-B" protein with the substrate "B", as the mutant "AGT-A" protein (or wild type AGT) is already inactivated by substrate "A". Likewise, a mixture containing mutant "AGT-B" and mutant "AGT-A" (or wild type AGT) may be simultaneously incubated with substrate "A" and substrate "B", leading to preferential reaction of mutant "AGT-A" (or wild type AGT) with substrate "A" and preferential reaction of mutant "AGT-B" with substrate "B", provided that the reactivity of mutant "AGT-A" (or wild type AGT) for substrate "A" under the concentrations selected will lead to preferential reaction of mutant "AGT-A" (or wild type AGT) with substrate "A" even in the presence of the selected concentration of substrate "B". The two different substrates "A" and "B" might carry, for example, the two compounds of a fluorescence resonance energy transfer pair (FRET), or one fluorophore and one quencher for a proximity assay.

The invention relates also to a method for detecting and/or manipulating a protein of interest wherein the protein of interest is incorporated into a fusion protein with an AGT mutant, the AGT fusion protein is contacted with particular AGT substrates carrying a label, and the AGT fusion protein is detected and optionally further manipulated using the label in a system designed for recognising and/or handling the label, which makes use of the preferential (or particularly low) reactivity of one AGT mutant with one substrate, for example, as described in the preceding paragraph. In particular the invention relates to the method wherein an AGT fusion protein mixture containing the AGT fusion protein of the protein of interest and the AGT mutant and a further AGT fusion protein is contacted with a particular substrate, for which either the AGT mutant or the further AGT is selective, the mixture is treated with a further substrate, and the AGT fusion protein of the protein of interest and the AGT mutant is detected and optionally further manipulated using the label in a system designed for recognising and/or handling the label. The further substrate may be added to the AGT fusion protein mixture after complete reaction of the mixture with the particular substrate, or together with the particular substrate.

More particularly, the invention relates to these methods wherein the label of the particular substrate interacts with the label of the further substrate, for example wherein the labels are compounds of a fluorescence resonance energy transfer pair (FRET) or one fluorophore and one quencher for a proximity assay.

EXAMPLES

Abbreviations Used:
AGTM=AGT mutant with modifications Cys62Ala, Gln115Ser, Gln116His, Lys125Ala, Ala127Thr, Arg128Ala, Gly131Lys, Gly132Thr, Met134Leu, Arg135Ser, Cys150Asn, Ser151Ile, Ser152Asn, Asn157Gly, Ser159Glu, truncated after Gly182
BG-Bt=$O^6$-(4-aminomethyl-benzyl)-guanine coupled to biotin
Bg-Cy3=$O^6$-(4-aminomethyl-benzyl)-guanine coupled to Cy3
DTT=1,4-dithiothreitol
GST=glutathione-S-transferase (from *Schistosoma japonicum*)
HEPES=2-[4-(2-hydroxyethyl)-1-piperazinyl]ethanesulfonic acid
IPTG=isopropyl β-D-1-thiogalactopyranoside
PEG=polyethylene glycol
PMSF=phenylmethanesulfonyl fluoride SDS-PAGE=sodium dodecyl sulphate polyacrylamide gel electrophoresis Example 1

Mutations Lys125Ala, Ala127Thr, Arg128Ala, Asn157Gly, Ser159Glu

Two partially overlapping regions of the PGEG-hAGT gene, an AGT containing the mutations Asn157Gly, Ser159Glu (Juillerat et al., Chem Biol 10:313-317, 2003), are amplified with the primers SEQ ID NO:3, SEQ ID NO:6 and SEQ ID NO:4, SEQ ID NO:5 in separate reactions. With respect to their partial complementarity, these two parts are assembled in a further PCR reaction, and amplified with the primers SEQ ID NO:3 and SEQ ID NO:4 to give rise to the complete gene now further containing the mutations Lys125Ala, Ala127Thr, Arg128Ala. The gene is subsequently cloned between the BamH1 and EcoR1 sites of the expression vector pGEX-2T (Pharmacia). This allows the expression of the inserted gene as a C-terminal fusion to the GST protein, the gene of which is provided by the vector.

Protein expression from this vector is carried out in *E. coli* strain BL21. An exponentially growing culture is induced with 0.5 mM IPTG, and the expression is carried out for 3.5 h at 24° C.

Purification: The harvested cells are resuspended in a buffer containing 50 mM phosphate, 0.5 M NaCl, 1 mM DTT, supplemented with 1 mM PMSF and 2 µg/ml aprotinin, and disrupted by lysozyme and sonification. The cell debris are separated by centrifugation at 40000×g. The extract is applied to pre-equilibrated glutathione sepharose (Amersham) which is then washed with 20 bed volumes (50 mM phosphate, 0.5 M NaCl, 1 mM DTT). The mutated GST-AGT fusion protein is eluted with 10 mM reduced glutathione in 50 mM Tris·HCl pH 7.9. The purified protein is dialyzed against 50 mM HEPES pH 7.2; 1 mM DTT; 30% glycerol and then stored at −80° C.

Determination of protein yield: Purity and relative amounts of the GST-AGT fusion proteins are compared by running samples on SDS-PAGE. UV spectra of the pure fractions are recorded using a Perkin Elmer Lambda 10. For protein samples containing no significant amount of DNA, the extinction at 280 nm as a measure of protein content is compared to that of wild type hAGT or PGEG-hAGT that were purified under the same conditions.

For comparing the DNA binding properties of the protein in vitro, the harvested cells are resuspended, and the GST fusion protein is purified following the same method but in a buffer containing 50 mM phosphate, 0.1 M NaCl, 1 mM DTT. In the dialysed samples, the amount of subsequently co-purified DNA is estimated by UV spectroscopy. Spectra are recorded using a Perkin Elmer Lambda 10. The content of DNA corresponds to the ratio of the extinctions at 280 and 260 nm. This value is compared to the one obtained on purifying wild type hAGT or PGEG-hAGT, respectively.

Activity assay: Purified mutated GST-AGT is incubated in vitro with a biotinylated $O^6$-benzylguanine (BG-Bt, substance 3a of Juillerat et al., Chem Biol 10:313-317, 2003). In a total reaction volume of 80 µl, 0.2 µM GST-AGT are incubated with 1 µM substrate in 50 mM HEPES pH 7.2 and 1 mM DTT at room temperature. At several points of time an aliquot is quenched with 1 mM $O^6$-benzylguanine (Sigma) in SDS-Laemmli buffer and subjected to Western blotting analysis (neutravidin-peroxidase conjugate (PIERCE), Renaissance reagent plus (NEN)). The intensity of the corresponding bands is quantified by a Kodak Image Station 440.

In vivo localization: The mutated AGT (Lys125Ala, Ala127Thr, Arg128Ala, Asn157Gly, Ser159Glu) gene is amplified with the primers SEQ ID NO:7, SEQ ID NO:8 and cloned between the NheI and BamHI sites of the vector pEGFP-Nuc (Clontech). This construct is transfected into CHO-cells deficient in endogenous AGT (B. Kaina et al., Carcinogenesis 12, 1857-1867, 1991). After transient expression of the AGT during 24 h, the cells are incubated with 0.5 µM substance 4 of Juillerat et al., Chem Biol 10:313-317, 2003 for 5 minutes and washed with PBS during 30 minutes. The cells are imaged by Laser scanning confocal microscopy using a 488 nm argon/krypton laser line on a Zeiss LSM 510 microscope (Carl Zeiss AG) with a water (1.2 numerical aperture) objective.

In *E. coli*, the GST fusion of mutant AGT Lys125Ala, Ala127Thr, Arg128Ala, Asn157Gly, Ser159Glu yields at least three times more soluble protein than the PGEG-hAGT. It shows at least ten times reduced DNA binding, and retains activity towards $O^6$-benzylguanine substrates. In CHO cells, the fluorescently labeled mutated AGT is distributed throughout the cytoplasm, no preferential nuclear localization can be detected.

Example 2

Mutations Cys62Ala, Lys125Ala, Ala127Thr, Arg128Ala, Asn157Gly, Ser159Glu

The mutant AGT gene of Example 1 is amplified and cloned as described in Example 1 with the oligonucleotides SEQ ID NO:3, SEQ ID NO:10 and SEQ ID NO:4, SEQ ID NO:9 causing the further mutation Cys62Ala in the gene upon their incorporation by PCR. Protein expression, purification and determination of yield is carried out as described in Example 1. The mutant gene is PCR amplified with the primers SEQ ID NO:11, SEQ ID NO:12 that contain SfiI restriction sites to subclone the gene in fusion to the g3 protein of filamentous phage in the vector pAK100 (Krebber et al., J Immunol Methods 201:35-55, 1997). When expressing the gene in the non-suppressor strain *E. coli* BL21, the amber stop codon terminates translation after the AGT gene. Therefore, periplasmic expression of mutant AGT protein from this vector is carried out as described in Example 1. The harvested cells are resuspended in a buffer containing 50 mM phosphate, 1 M NaCl, 1 mM DTT, supplemented with 1 mM PMSF and 2 µg/ml aprotinin and disrupted by lysozyme and sonification. The cell debris are separated by centrifugation at 40000×g. The supernatant is directly subjected to quantification of protein yield via SDS-PAGE and activity assays as described in Example 1.

The mutant Cys62Ala, Lys125Ala, Ala127Thr, Arg128Ala, Asn157Gly, Ser159Glu retains activity towards $O^6$-benzylguanine substrates. The yield of soluble GST fusion protein from this mutant AGT is at least two times higher than that of mutant Lys125Ala, Ala127Thr, Arg128Ala, Asn157Gly, Ser159Glu of Example 1. The yield of active AGT mutant from expression in the periplasm of *E. coli* is at least three times higher than that of PGEG-hAGT.

Example 3

Truncation at 182, Asn157Gly, Ser159Glu

The PGEG-hAGT gene (Asn157Gly, Ser159Glu, see Juillerat et al., Chem Biol 10:313-317, 2003) is amplified with primers SEQ ID NO:3, SEQ ID NO:13 to introduce a stop-codon and a EcoRI site after codon 182, and subsequently cloned between the BamH1 and EcoR1 sites of the expression vector pGEX2T (Pharmacia). Protein expression, purification and estimation of expression yield is carried out as described in Example 1.

The truncated PGEG-hAGT mutant retains activity towards $O^6$-benzylguanine substrates. The yield of soluble mutant GST-AGT fusion protein is at least two times higher than that of mutant PGEG-hAGT.

Example 4

Mutations Gly131Lys, Gly132Thr, Met134Leu, Arg135Ser, Asn157Gly, Ser159Glu

The PGEG-hAGT gene (Asn157Gly, Ser159Glu, see Juillerat et al., Chem Biol 10:313-317, 2003) is PCR-amplified with the primers SEQ ID NO:11, SEQ ID NO:15 and SEQ ID NO:12, SEQ ID NO:14 and assembled as described in Example 1. The primers contain the nucleotide mixtures NNK (N=A, C, G or T; K=G or T) at positions corresponding to the codons 131, 132, 134, 135 of the hAGT gene. The gene is cloned in fusion to the g3 protein of filamentous phage in the vector pAK 100 via SfiI restriction sites. The resulting gene library is used for phage display.

Production of phages of this library is carried out in *E. coli* JM101 cells. An exponential culture is superinfected with helper phage and grown overnight at 24° C. The supernatant of this culture is incubated with 1 □M digoxigeninylated $O^6$-benzylguanine (substance 2 of Juillerat et al., Chem Biol 10:313-317, 2003) for 6 minutes. In subsequent selection rounds, the reaction time is decreased to 90 seconds and 45 seconds, respectively, and the concentration of substrate is decreased to 10 nM to increase selection pressure. Phages are purified from this reaction by precipitation with 4% PEG/3% NaCl. The phages carrying mutant AGT that is now covalently labeled with digoxigenin are isolated by incubation with magnetic beads coated with anti-digoxigenin antibodies (Roche Diagnostics), and used for re-infection of bacteria.

Selected AGT mutants are subcloned into pGEX2T, expressed, purified and characterized as described in Example 1. Discrimination between $N^9$ substituted and $N^9$ unsubstituted $O^6$-benzylguanine substrates is evaluated by competition experiments for purified mutated GST-AGT in vitro with $N^9$-substituted and N'-unsubstituted $O^6$-benzylguanine. Aliquots of 0.2 µM GST-AGT are incubated with varying concentrations of $N^9$ substituted substrate (0, 0.5, up to 100 □M) and 0.5 □M biotinylated $O^6$-benzylguanine (BG-Bt, substance 3a of Juillerat et al., Chem Biol 10:313-317, 2003) in 50 mM HEPES pH 7.3 and 1 mM DTT at room temperature. After 45 min reactions are quenched by the addition of SDS-Laemmli buffer and heat denaturation. Samples are subjected to SDS-PAGE and Western blotting analysis (neutravidin-peroxidase conjugate (PIERCE), Renaissance reagent plus (NEN)). The intensity of the corresponding bands is quantified by a Kodak Image Station 440.

The yield of soluble GST fusion protein from this mutant AGT is at least two times higher than that of PGEG-hAGT. The mutant AGT shows at least twofold further increased activity towards $O^6$-benzylguanine substrates. Reactivity towards $O^6$-alkyl-$N^9$-deoxyribosylguanine or $N^9$-cyclopentyl-$O^6$-benzylguanine is reduced at least 10 fold, for particular clones at least 100 fold compared to PGEG-hAGT. Reactivity with oligonucleotides, e.g. the oligonucleotide SEQ ID NO:2 wherein guanine in position 14 carries an $O^6$-benzyl group, is reduced at least 1000 fold compared to PGEG-hAGT.

Example 5

Mutations Gln115Ser, Gln116His, Cys150Asn, Ser151Ile, Ser152Asn, Asn157Gly, Ser159Glu A library of hAGT mutants is constructed as described in Example 4 from three PCR fragments using the primers combinations SEQ ID NO:11, SEQ ID NO:17; SEQ ID NO:16, SEQ ID NO:19 and SEQ ID NO:12, SEQ ID NO:18 in three separate PCR reactions. The gene is assembled from the partially overlapping fragments, two of them containing the randomized nucleotide mixtures NNK at positions corresponding to codons 115-116 and 150-152, respectively. Phage display selections are carried out as described in Juillerat et al., Chem Biol 10:313-317, 2003. Selected proteins are subcloned into pGEX, expressed, purified and characterized as described in Example 1. Periplasmic expression is carried out as described in Example 2.

The yield of soluble GST fusion protein from this mutant AGT is at least two times higher than that of PGEG-hAGT. The mutant AGT retains activity towards $O^6$-benzylguanine substrates. The yield of active AGT mutant from expression in the periplasm of *E. coli* is at least two times higher than that of PGEG-hAGT.

Example 6

Mutations Cys62Ala, Gln115Ser, Gln116His, Lys125Ala, Ala127Thr, Arg128Ala, Gly131Lys, Gly132Thr, Met134Leu, Arg135Ser, Cys150Asn, Ser151Ile. Ser152Asn, Asn157Gly, Ser159Glu, Truncation at 182, "AGTM"

The mutations from Examples 2, 3, 4, 5 are combined: Four overlapping fragments of the mutant AGT gene (Cys62Ala, Lys125Ala, Ala127Thr, Arg128Ala, Asn157Gly, Ser159Glu) from Example 1 are amplified using the primer combinations SEQ ID NO:3, SEQ ID NO:23; SEQ ID NO:21, SEQ ID NO:22; SEQ ID NO:20, SEQ ID NO:25 and SEQ ID NO:24, SEQ ID NO:13 assembled to the gene and subcloned into pGEX2T as described under Example 1. The mutant AGT ("AGTM") is expressed and purified and characterized as described under Example 1.

The solubility of AGTM or an AGTM fusion protein in vitro is measured by determining the amount of protein that remains in the soluble fraction after overnight incubation of purified samples at 4 or up to 37° C. at one or several concentrations established in a suitable buffer (e.g. 100 mM NaCl, 20 mM Tris, pH 8.0, 20% Glycerol), and it is compared to that of wild type AGT or to known AGT mutants such as "PGEG-hAGT" (Juillerat et al., Chem Biol 10:313-317, 2003).

The mutant AGTM shows an expression rate further increased at least twofold compared to the mutants described in the Examples 1 through 5 and has an at least fourfold increased solubility in vitro when compared to wild type AGT. It retains the reactivity towards $O^6$-benzylguanine, but shows significantly reduced reactivity at least by a factor of 10 with $N^9$-substituted $O^6$-alkylguanine derivatives and reduced reactivity at least by a factor of 100 with DNA substrates.

Stability under oxidizing conditions: The mutant gene is PCR amplified with the primers SEQ ID NO:11 and SEQ ID NO:28 to subclone the gene into pAK100, as described in Example 2. Protein expression and cell lysis is done as described in Example 2 to obtain cleared cell lysates. To compare the reactivity of PGEA-hAGT (Juillerat et al., Chem Biol 10:313-317, 2003) and the mutant, samples are incubated with 1 □M BG-Bt for 50 min, quenched with SDS- Laemmli buffer and analyzed by western blotting using neutravidin peroxidase conjugate (Pierce) or a monoclonal mouse anti-FLAG IgG antibody (M2, Sigma) and a secondary anti-mouse-IgG::HRP conjugate, and Renaissance reagent plus (NEN). The blot is visualized on a Kodak Image station 440. The anti-FLAG IgG antibody is used to estimate the total amount of soluble AGT protein, whereas neutravidin quantifies the reactive portion of it. The expected molecular weight of the AGT mutants is 21 and 24 kDa, respectively.

Periplasmic expression leads to two to threefold more AGTM but at least tenfold more active protein of this mutant than for the mutant PGEA-hAGT (normalized to protein yield).

Reactivity against DNA-based substrates measured with a BG-Cy3 assay: BG-Cy3 is prepared by reacting the previously described $O^6$-(4-aminomethyl-benzyl)guanine (Keppler et al., NatureBiotechnol. 21:86-89, 2003) with the commercially available N-hydroxysuccinimide ester of Cy3, (Cy3-NHS, Amersham). The coupling reaction is performed at ambient temperature in N,N-dimethylformamide in the presence of 1 eq. of triethylamine. The BG-Cy3 conjugate is purified by reversed-phase HPLC on a C18-column by using linear gradients from 0.1% trifluoroacetic acid to acetonitrile. After solvent evaporation BG-Cy3 is dissolved in dimethyl sulfoxide and stored at −20° C. For measuring the reactivity with DNA-based substrates, a reaction mixture containing different concentrations (0 to 5 $\square$M) of oligonucleotide SEQ ID NO:2 (modified in position 14), GST-AGT fusion protein at 0.2 $\square$M and BG-Cy3 at 0.5 CM in reaction buffer (50 mM HEPES, pH 7.2, 1 mM DTT, 200 mg/ml BSA) is incubated in microtiterplates. Fluorescence of the Cy3 derivative (excitation 519 nm, emission at 572 nm) is measured on a Spectramax Gemini plate reader (Molecular Devices).

The mutant AGTM shows no reduction of its reaction with BG-Cy3 in presence of up to 5 $\square$M BG-modified oligonucleotide (FIG. 1A). The activity of PGEG-hAGT is below background level (less than 3%) in presence of 0.5 $\square$M (or more) BG-modified oligonucleotide (FIG. 1B).

DNA binding: DNA binding is measured as inhibition by DNA of the reaction of AGT mutants with BG derivatives. The reaction rate of AGT mutants in a reaction mixture containing salmon sperm DNA (25 $\square$g/ml) instead of oligonucleotide is measured with the BG-Cy3 assay. The reaction rate is determined by fitting the obtained data to a monoexponential increase to maximum.

The reaction rate of AGTM to BG-Cy3 is unchanged in presence of DNA, whereas the rate of PGEG-hAGT to BG-Cy3 is reduced 5 fold in presence of DNA.

Stability after reaction: The vector pBAD/H is A (Invitrogen) is modified by cloning synthetic oligonucleotides (SEQ ID NO:29 and SEQ ID NO:30) between the NcoI and HindIII sites to include a 12×His-tag and SbfI and AscI cloning sites. The gene of AGTM is amplified with primers SEQ ID NO:31 and SEQ ID NO:32 and cloned between the SbfI/AscI sites into this vector. Wild type AGT and mutant AGT (Lys125Ala, Ala127Thr, Arg128Ala, Asn157Gly, Ser159Glu) are amplified with primers SEQ ID NO:31 and SEQ ID NO:33 and cloned into this vector. Protein expression is carried out in E. coli strain Top 10. An exponentially growing culture is induced with 0.2% arabinose, and the expression is carried out for 16 hours at 28° C. The cells are lysed by adding buffer to 10 ml/g containing 0.5 M NaCl, 80 mM imidazole, 1% Triton, 250 $\square$M PMSF, 1 mM $\square$-mercaptoethanol, 5 mg/ml lysozyme, 20 $\square$g/ml DNase and stirring for 45 min. The supernatant after centrifugation at 10,000 g for 30 min is loaded to a equilibrated Ni-NTA (Qiagen) column, washed with 20 column volumes of 0.5 M NaCl, 100 mM imidazole, 1 mM $\square$-mercaptoethanol, followed by 3 volumes of 0.25 M NaCl, 100 mM imidazole, 20% glycerol. The protein is eluted with 0.25 M NaCl, 400 mM imidazole, 20% glycerol. After adding 1 mM DTT, the protein is stored at −80° C.

The AGT proteins at 10 $\square$M are quantitatively reacted with fluorescein-modified $O^6$-benzyl-guanine (substance 5 of Juillerat et al, Chem Biol 10:313-317, 2003, BG-FL, 20 $\square$M) and purified over a size exclusion column (Econopac 10 DG, Bio-Rad) and incubated for 7 days. At various timepoints, aliquots are centrifuged at 25,000 g, and 1% SDS is added to the supernatant. The fluorescence of the supernatant is measured with a Victor2 fluorescence plate reader (Perkin Elmer, excitation/emission at 485/535 nm).

In contrast to hAGT or mutant (Lys125Ala, Ala127Thr, Arg128Ala, Asn157Gly, Ser159Glu) which loses about 60% of soluble fluorescent protein over 7 days, the labeled mutant AGTM remains stable in solution over more than 7 days.

Reactivity of AGT towards $N^9$-modified $O^6$-benzylguanine derivatives: The experiment is based on the BG-Cy3 assay. Upon reaction of AGT with BG-Cy3, an increase of fluorescence emission intensity of Cy3 by a factor 2-3 can be observed. The reactivity of AGTM (Example 6) versus PGEG-hAGT (Juillerat et al. 2003, containing the mutations N157G, S159E) towards the compounds $N^9$-isobutyl-$O^6$-benzylguanine, $N^9$-propyl-$O^6$-benzylguanine or $N^9$-nitril-$O^6$-benzylguanine, is investigated by preincubating samples of 10 $\square$M of GST-AGT fusion protein with 100 $\square$M of these substances in reaction buffer (50 mM HEPES, pH 7.2, 100 mM NaCl, 0.1% Tween-20, 1 mM DTT) for 15 min at room temperature. Subsequently, BG-Cy3 (20 $\square$M final concentration) is added and the reaction is incubated for an additional 1 h at room temperature. Samples are diluted 1:20 in reaction buffer and transferred to microtiterplates. Fluorescence intensity of the Cy3 fluorophore (excitation: 519 nm, emission: 572 nm) is measured with the Spectra Max Gemini microplate reader (Molecular Devices).

Figure 3:
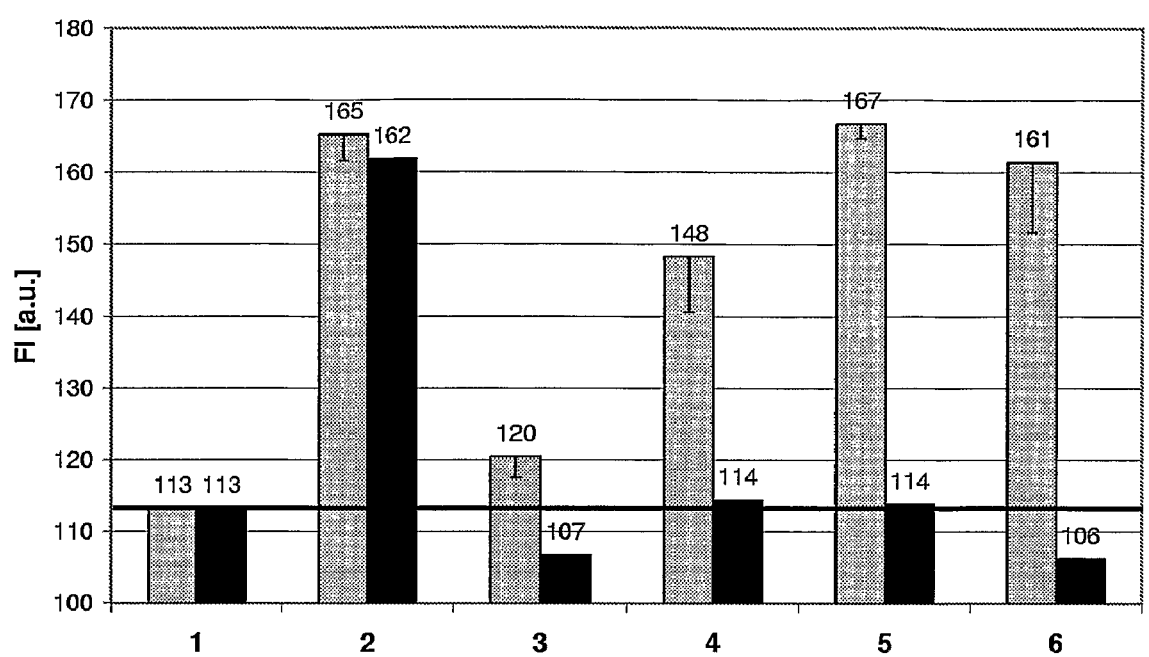
FIG. 3: Reactivity of AGT mutants with $N^9$-modified BG derivatives. 10 □M AGTM (grey bars) or PGEG-hAGT (black bars) were preblocked with 100 □M $N^9$-modified BG derivatives (see list below), and subsequently labeled with 20 □M BG-Cy3. After 1 h reaction time, fluorescence intensity (FI) indicated in arbitrary units [a.u.] at 595 nm is measured. The black bold line is set at the reading for condition 1 corresponding to background fluorescence of the fluorophore not attached to protein. Values above this line indicate slow or incomplete reaction with $N^9$-modified BG-derivative.

Both AGT mutants are efficiently preblocked with BG (100 $\square$M, 15 min reaction time) (FIG. 3, No. 3). 5% of AGTM remains active after preblocking with BG (grey bar). A significant difference in reactivity between AGTM and PGEG-hAGT towards $N^9$-modified BG derivatives is observed. AGTM reacts to an extent of 1% to 10% with the $N^9$-modified BG derivatives (FIG. 3, Nos. 4, 5, 6, grey bars). Contrary to AGTM, PGEG-hAGT reacts efficiently with all three $N^9$-modified BG derivatives. No fluorescence increase above background is observed upon subsequent incubation with BG-Cy3 indicating complete reaction with the $N^9$-substituted compounds (FIG. 3, Nos. 4, 5, 6, black bars).

Example 7

Reaction of Two Different Variants of AGT Present in One Biological Sample with Two Different Substrates The mutant AGT of Example 6 (AGTM) is PCR-amplified with the primers SEQ ID NO:26 and SEQ ID NO:27, and is subcloned into pET15b via NdeI and BamHI. Gene expression from this vector is carried out in E. coli strain BL21 (DE3) as described under Example 1 leading to a protein with an N-terminally fused His-tag that is coded for by the vector. Cells are harvested and extracted as described under Example 1 in extract buffer containing 0.5 M NaCl, 10 mM imidazole, 50 mM phosphate pH 8.0. The extract containing the protein is applied to pre-equilibrated Ni-NTA-Sepharose (Qiagen), which is then washed with 20 bed volumes of the buffer containing 20 mM imidazole. The His-tagged protein is eluted with buffer containing 250 mM imidazole. The purified protein is dialysed, stored and later on characterized as described under Example 1.

Within the experiment two tags with different size for the two AGT proteins are used: The His-tagged AGTM (~20 kDa) and GST-hAGT (cloned and prepared as described in Example 1, but starting with the wild type hAGT gene, ~48 kDa) are diluted to 0.2 µM and 1.2 µM final concentration, respectively, in reaction buffer containing 50 mM HEPES, 1 mM DTT, 200 mg/mL BSA (pH 7.3). The sample is incubated with a mixture of substrates $N^9$-cyclopentyl-$O^6$-bromophenyl-guanine (CPTG; 0, 5 and 10 µM final concentrations) and biotinylated $O^6$-benzylguanine (BG-Bt, 5 µM final concentration) for 30 minutes. The reaction is quenched by addition of SDS-Laemmli buffer and subjected to Western blotting analysis (Example 1). As the two AGT variants have different masses, the two proteins can be separated on an acrylamide gel and analyzed independently. A high specificity of CPTG towards GST-hAGT is observed. At the same concentration (both substrates at 5 µM final concentration), 95% of GST-hAGT reacts with CPTG, versus only 5% of His-tagged AGTM.

Substrate CPTG is available by cyclopentenylation of position N-9 of 6-chloroguanine with cyclopentenyl methyl carbonate, reduction to 6-chloro-$N^9$-cyclopentyl-guanine, and reaction with 4-bromo-2-hydroxymethylthiophene in the presence of a tertiary amine.

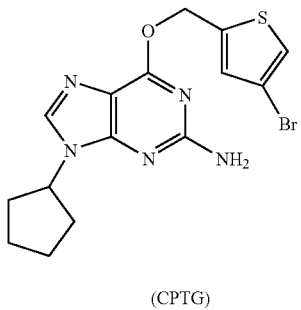

(CPTG)

In a further experiment, the mutant AGTM as described in Example 6 is amplified with the primers SEQ ID NO:34 and SEQ ID NO:36 and cloned between the NheI and BglII sites of the vector pEGFP-Nuc. The yeast □-galactosidase gene is amplified with the primers SEQ ID NO:37 and SEQ ID NO:38 and subcloned into this vector via BglII/BamHI to result in a vector with an AGTM-□-Gal fusion gene. The hAGT gene is amplified by the principle described under Example 1 with the primers SEQ ID NO:39, SEQ ID NO:40, SEQ ID NO:34, and SEQ ID NO:35 and cloned via NheI/BglII into pEGFP-Nuc to result in an AGT-NLS3 fusion gene coding for the mutation Gly160Trp. After transient expression of both AGT mutants in parallel, the cells are incubated with 5 □M CPTG for 10 min and subsequently with 5 □M of substance 4 of Juillerat et al., Chem Biol 10:313-317, 2003, for 20 min. The cells are washed and imaged as described under Example 1.

In CHO cells, the cytoplasmically localized AGTM-□-galactosidase fusion protein is selectively fluorescence labeled by reaction with the fluorescent substrate substance 4. No significant labeling of the other AGT fusion protein in the nucleus is observed. It is concluded that the AGT (Gly160Trp) efficiently reacts with CPTG inside cells and therefore cannot be labeled with the fluorescent substrate afterwards. The mutant of Example 6 (AGTM) remains reactive to the fluorescent substrate after pre-incubation with CPTG inside cells and therefore does not react with CPTG in the first step.

Example 8

Further Mutations in the Compound Cys62Ala, Gln115Ser, Gln116His, Lys125Ala, Ala127Thr, Arg128Ala, Gly131Lys, Gly132Thr, Met134Leu, Arg135Ser, Cys150Asn, Ser151Ile, Ser152Asn, Asn157Gly, Ser159Glu, Truncation at 182

A) Error prone PCR: The gene for AGTM of Example 6 from vector pAK100 is amplified by an error prone PCR reaction that is spiked with 120 □M (6-(2-deoxy-β-D-erythro-pento-furanosyl)-3,4-dihydro-6H, 8H-pyrimido[4,5-c][1,2]oxazin-2-one)-5'-triphosphate and 480 □M 2'-deoxy-8-oxo-guanosine-triphosphate (both from Trilink Biotechnologies) with the primer SEQ ID NO:42 and the biotinylated primer SEQ ID NO:41 using Taq-polymerase. The product is captured on streptavidin coated beads (Dynabeads M-280, Dynal) and then amplified with the primers SEQ ID NO:43 and SEQ ID NO:44 by standard PCR.

B) Saturation mutagenesis, Region 150-154: The gene for AGTM (mutant of Example 6) is amplified with the primers SEQ ID NO:11, SEQ ID NO:45, SEQ ID NO:46 and SEQ ID NO:28 by PCR as described in Example 1, and subcloned via SfiI into pAK100. The primers contain the nucleotide mixtures NNK (N=A, C, G or T; K=G or T) at positions corresponding to the codons 150-154 of the hAGT gene.

C) Saturation mutagenesis, Region 31-35: The gene coding for AGTM (mutant of Example 6) is amplified with the primers SEQ ID NO:11, SEQ ID NO:48, SEQ ID NO:47 and SEQ ID NO:28 by PCR as described in Example 1, and subcloned via SfiI into pAK100. The primer 47 contains the nucleotide mixtures NNK (N=A, C, G or T; K=G or T) at positions corresponding to the codons 31 to 35 of the hAGT gene, primer 48 the mixtures MNN (M=C or A) for the antisense strand.

The amplified products are cloned in fusion to the g3 gene of filamentous phage in the vector pAK100 via SfiI restriction sites. The resulting gene libraries are used for phage display as described under Example 4. The mutants of the libraries are selected with 5 to 50 nM of BG-Bt for 10 min. Selected mutants are subcloned into pGEX using the primers SEQ ID NO:3 and SEQ ID NO:13. The reaction rate of mutant AGTs is determined as described in Example 6, Reactivity against DNA-based substrates (BG-Cy3 assay).

Combination of mutations: Mutations from selections found to improve the reaction rate with BG derivatives are combined by PCR as described in Example 1 with the primers SEQ ID NO:3 and SEQ ID NO:13 using one mutant gene as template and including further mutations in primer sequences that mismatch at the point of the mutation. Each of the two mutagenic primers is chosen to anneal to one of the complementary strands respectively, overlapping the mutation, with a length sufficient for hybridizing below 60° C. The annealing temperature is calculated by supposing contributions of 4° C. for each G/C pair and 2° C. for each A/T pair. The resulting gene is subcloned into pGEX as described in Example 1. The mutant AGT proteins are prepared and characterized as described under Examples 1, 4 and 6.

AGT mutants carrying the combined mutations from these selections show the advantageous properties described for mutants of Example 1 to 6. The mutants have an expression rate comparable to the mutants described in the Examples 1 through 5 and have an at least fourfold increased solubility in vitro when compared to wild type AGT. They show significantly reduced reactivity at least by a factor of 10 with $N^9$-substituted $O^6$-alkylguanine derivatives, reduced interaction and reactivity at least by a factor of 100 with DNA or DNA substrates respectively. The yield of active AGT mutant from expression in the periplasm of E. coli is at least five times higher than that of PGEG-hAGT. In CHO cells, the fluorescently labeled mutated AGT is distributed throughout the cytoplasm, no preferential nuclear localization can be detected. Furthermore, these AGT mutants show considerably increased reactivity towards $O^6$-benzylguanine substrates when compared to wild type hAGT (see Table 1).

TABLE 1

Reaction rate of AGT mutants having all mutations of AGTM (mutant of Example 6) and additionally those listed.

| Mutations | Relative reaction rate | |
|---|---|---|
| Lys32Ile, Leu33Phe, ☐Leu34, Asn150Gly, Ile151Gly, Asn152Asp, Ala154Asp | 51.09 | p. |
| Lys32Ile, Leu33Phe, Asn150Gly, Ile151Gly, Asn152Asp, Ala154Asp | 45.45 | p. |
| Lys32Ile, Leu33Phe, Asn150Val, Ile151Ser, Asn152Arg, Gly153Asp, Ala154Asp | 44.91 | p. |
| Lys32Ile, Leu33Phe, Ala154Thr | 33.89 | p. |
| Asn150Val, Ile151Ser, Asn152Arg, Gly153Asp, Ala154Asp | 21.26 | p. |
| Asn150Gly, Ile151Gly, Asn152Asp, Ala154Asp | 19.80 | p. |
| Asn150Glu, Ile151Gly, Asn152Glu, Ala154Arg | 18.42 | p. |
| Asn150Val, Ile151Asn, Asn152Asp, Gly153Leu, Ala154Asp | 15.67 | p. |
| Lys8Thr, Thr127Ala, Ala154Thr, His174Arg | 15.66 | x. |
| Asn150Glu, Ile151Ser, Asn152His, Ala154Lys | 15.43 | p. |
| Ala154Thr | 14.90 | p. |
| Lys104Glu, Thr127Ala, Ala154Thr | 12.34 | x. |
| Asn150Glu, Ile151Gly, Asn152Trp, Gly153Asn, Ala154Glu | 11.97 | p. |
| Asn150Glu, Ile151Gly, Asn152Arg, Gly153Glu, Ala154Arg | 11.20 | p. |
| Lys32Ile, Leu33Phe, Gly182Val | 9.48 | x. |
| Asn150Asp | 7.19 | p. |
| Thr127Ala | 5.83 | p. |
| AGTM | 2.72 | p. |
| Wild type hAGT | 1 | p. |

Reaction rates were determined by the BG-Cy3 activity assay and divided by the value obtained with this assay for wild type hAGT ($k_{obs}$=116 M$^{-1}$ cm$^{-1}$). For the activity assay purified GST fusion proteins were used for mutants marked with "p." (prepared as described under Example 1); periplasmic extracts were used for mutants marked with "x." (prepared as described under Example 2).

The invention claimed is:

1. An isolated mutant $O^6$-alkylguanine-DNA alkyltransferase (AGT) of the wild type human AGT encoded by SEQ ID NO: 1, wherein between 6 and 25 amino acids are substituted by other amino acids; and/or 2 to 5 consecutive amino acids at position one, two or three are deleted or added; and/or 1 to 4 amino acids at the N-terminus are deleted; and/or 1 to 40 amino acids at the C-terminus are deleted, and wherein two or more modifications are selected from the group consisting of
 (A) Cys62 replacement by Ala or Val;
 (B) Gln115-Gln116 replacement by Ala-Asn, Asn-Asn, Ser-His, Ser-Ser, Pro-Pro, Pro-Ser, Pro-Thr, or Thr-Ser;
 (D) Gly131-Gly132/Met134-Arg135 replacement by Val-His/Leu-Arg, Lys-Thr/Leu-Ser, Gln-Val/Leu-Ser, or Met-Thr/Met-Val, or Gly131-Gly132/Met134 replacement by Val-His/Leu;
 (E) Cys150-Ser151-Ser152 replacement by Asn-Ile-Asn, Pro-Leu-Pro, Pro-Arg-Thr, Ser-Phe-Pro-, or Ser-His-Thr-, or Cys150-Ser151 replacement by Phe-Asn or Arg-Asn, or Cys150/Ser152 replacement by His/Thr, Leu/Asn, Leu/Asn, Leu/Pro or Pro/Leu, or Cys150 replacement by Ser or Thr;
 (F) Pro140/Asn157/Ser159 replacement by Phe/Arg/Glu, or Pro 140/Asn157/Gly160 replacement by Met/Trp/Val, or Asn157/Ser159-Gly160 replacement by Gly/Glu-Ala, Gly/Asn-Trp, Pro/Gln-Cys or Gly-Gln-Trp, or Asn157/Ser159 replacement by Gly/Glu, or Asn157 replacement by Gly or Arg; and
 (G) truncation after Gly182; and optionally 1 to 10 additional amino acid modifications.

2. The AGT mutant according to claim 1 wherein three or more modifications are selected from the group consisting of
 (A) Cys62 replacement by Ala or Val;
 (B) Gln115-Gln116 replacement by Ala-Asn, Asn-Asn, Ser-His, Ser-Ser, Pro-Pro, Pro-Ser, Pro-Thr, or Thr-Ser;
 (C) Lys125 replacement by Ala and Ala127-Arg128 replaced by Thr-Ala;
 (D) Gly131-Gly132/Met134-Arg135 replacement by Val-His/Leu-Arg, Lys-Thr/Leu-Ser, Gln-Val/Leu-Ser, or Met-Thr/Met-Val, or Gly131-Gly132/Met134 replacement by Val-His/Leu;
 (E) Cys150-Ser151-Ser152 replacement by Asn-Ile-Asn, Pro-Leu-Pro, Pro-Arg-Thr, Ser-Phe-Pro-, or Ser-His-Thr-, or Cys150-Ser151 replacement by Phe-Asn or Arg-Asn, or Cys150/Ser152 replacement by His/Thr, Leu/Asn, Leu/Asn, Leu/Pro or Pro/Leu, or Cys150 replacement by Ser or Thr;
 (F) Pro140/Asn157/Ser159 replacement by Phe/Arg/Glu, or Pro 140/Asn157/Gly160 replacement by Met/Trp/Val, or Asn157/Ser159-Gly160 replacement by Gly/Glu-Ala, Gly/Asn-Trp, Pro/Gln-Cys or Gly-Gln-Trp, or Asn157/Ser159 replacement by Gly/Glu, or Asn157 replacement by Gly or Arg; and
 (G) truncation after Gly182; and optionally 1 to 10 additional amino acid modifications.

3. The AGT mutant according to claim 1 wherein two or more modifications are selected from the group consisting of
 (A) Cys62 replacement by Ala;
 (B) Gln115-Gln116 replacement by Ser-His;
 (D) Gly131-Gly132/Met134-Arg135 replacement by Lys-Thr/Leu-Ser, or Gly131-Gly132/Met134 replacement by Val-His/Leu;
 (E) Cys150-Ser151-Ser152 replacement by Asn-Ile-Asn, or Cys150 replacement by Ser or Thr;
 (F) or Asn157/Ser159 replacement by Gly/Glu; and
 (G) truncation after Gly182;
and optionally 1 to 10 additional amino acid modifications.

4. The AGT mutant according to claim 1 wherein three or more modifications are selected from the group consisting of
 (A) Cys62 replacement by Ala;
 (B) Gln115-Gln116 replacement by Ser-His;
 (C) Lys125 replacement by Ala and Ala127-Arg128 replaced by Thr-Ala;
 (D) Gly131-Gly132/Met134-Arg135 replacement by Lys-Thr/Leu-Ser, or Gly131-Gly132/Met134 replacement by Val-His/Leu;
 (E) Cys150-Ser151-Ser152 replacement by Asn-Ile-Asn, or Cys150 replacement by Ser or Thr;
 (F) or Asn157 /Ser159 replacement by Gly/Glu; and
 (G) truncation after Gly182;
and optionally 1 to 10 additional amino acid modifications.

5. The AGT mutant according to claim 1 wherein three or more modifications are selected from the group consisting of
 (A) Cys62 replacement by Ala;
 (B) Gln115-Gln116 replacement by Ser-His;
 (C) Lys125 replacement by Ala and Ala127-Arg128 replaced by Thr-Ala;
 (E) Cys150-Ser151-Ser152 replacement by Asn-Ile-Asn, or Cys150 replacement by Ser or Thr;
 (F) or Asn157/Ser159 replacement by Gly/Glu; and
 (G) truncation after Gly182;
and optionally 1 to 10 additional amino acid modifications.

6. The AGT mutant according to claim 1 selected from mutants with modifications Cys62Ala, Lys125Ala, Ala127Thr, Arg128Ala, Asn157Gly, Ser159Glu, truncated after Gly182; Gly131Lys, Gly132Thr, Met134Leu, Arg135Ser, Asn157Gly, Ser159Glu; Gln115Ser, Gln116His, Cys150Asn, Ser151Ile, Ser152Asn, Asn157Gly, Ser159Glu; and Cys62Ala, Gln115Ser, Gln116His, Lys125Ala, Ala127Thr, Arg128Ala, Gly131Lys, Gly132Thr, Met134Leu, Arg135Ser, Cys150Asn, Ser151Ile, Ser152Asn, Asn157Gly, Ser159Glu, truncated after Gly182.

7. The AGT mutant according to claim 1 with modifications Cys62Ala, Gln115Ser, Gln116His, Lys125Ala, Ala127Thr, Arg128Ala, Cys150Asn, Ser151Ile, Ser152Asn, Asn157Gly, Ser159Glu, truncated after Gly182.

8. The AGT mutant according to claim 1 with modifications Cys62Ala, Gln115Ser, Gln116His, Lys125Ala, Ala127Thr, Arg128Ala, Gly131Lys, Gly132Thr, Met134Leu, Arg135Ser, Cys150Asn, Ser151Ile, Ser152Asn, Asn157Gly, Ser159Glu, truncated after Gly182 and optionally 1 to 10 additional amino acid modifications.

9. The AGT mutant according to claim 8 with modifications Cys62Ala, Gln115Ser, Gln116His, Lys125Ala, Ala127Thr, Arg128Ala, Gly131Lys, Gly132Thr, Met134Leu, Arg135Ser, Cys150Asn, Ser151Ile, Ser152Asn, Asn157Gly, Ser159Glu, truncated after Gly182 and optionally 3 to 7 additional amino acid modifications.

10. The AGT mutant according to claim 8 with modifications Cys62Ala, Lys125Ala, Ala127Thr, Arg128Ala, Gly131Lys, Gly132Thr, Met134Leu, Arg135Ser, Cys150Ser, Asn157Gly, Ser159Glu, truncated after Gly182 and optionally further mutations selected from Gln115Ser, Gln116His; Ser150Asn, Ser151Ile, Ser152Asn; Lys8Thr, Lys32Ile, Leu33Phe, Thr127Ala, Ser150Asp, Ser151Gly, Ala154Thr; Lys32Ile, Leu33Phe, Ser150Val, Ser152Arg, Gly153Asp, Ala154Asp; Lys32Ile, Leu33Phe, Ser150Gly, Ser151Gly, Ser152Asp, Ala154Asp; Ser150Val, Ala154Asp; Ser150Glu, Ser151Gly, Ser152Glu, Ala154Arg; Lys8Thr, Thr127Ala, Ala154Thr; Lys32Ile, Leu33Phe; Ala154Thr; Leu33Phe; Ser151Gly; Ser150Asp; Thr127Ala; and Lys32Ile, Leu33Phe, and deletion of Leu34.

11. The AGT mutant according to claim 1 with modifications Cys62Ala, Gln115Ser, Gln116His, Lys125Ala, Ala127Thr, Arg128Ala, Cys150Asn, Ser151Ile, Ser152Asn, Asn157Gly, Ser159Glu, truncated after Gly182 and optionally 1 to 10 additional amino acid modifications.

12. The AGT mutant according to claim 11 with modifications Cys62Ala, Gln115Ser, Gln116His, Lys125Ala, Ala127Thr, Arg128Ala, Cys150Asn, Ser151Ile, Ser152Asn, Asn157Gly, Ser159Glu, truncated after Gly182 and optionally 3 to 7 additional amino acid modifications.

13. The AGT mutant according to claim 1 with modifications Cys62Ala, Gln115Ser, Gln116His, Lys125Ala, Ala127Thr, Arg128Ala, Cys150Ser, Asn157Gly, Ser159Glu, truncated after Gly182 and optionally further mutations selected from Gln115Ser, Gln116His; Ser150Asn, Ser151Ile, Ser152Asn; Lys8Thr, Lys32Ile, Leu33Phe, Thr127Ala, Ser150Asp, Ser151Gly, Ala154Thr; Lys32Ile, Leu33Phe, Ser150Val, Ser152Arg, Gly153Asp, Ala154Asp; Lys32Ile, Leu33Phe, Ser150Gly, Ser151Gly, Ser152Asp, Ala154Asp; Ser150Val, Ala154Asp; Ser150Glu, Ser151Gly, Ser152Glu, Ala154Arg; Lys8Thr, Thr127Ala, Ala154Thr; Lys32Ile, Leu33Phe; Ala154Thr; Leu33Phe; Ser151Gly; Ser150Asp; Thr127Ala; and Lys32Ile, Leu33Phe, and deletion of Leu34.

14. The AGT mutant according to claim 1 with modifications Cys62Ala, Lys125Ala, Ala127Thr, Arg128Ala, Cys150Ser, Asn157Gly, Ser159Glu, truncated after Gly182.

15. The AGT mutant according to claim 1 with modifications Cys62Ala, Lys 125Ala, Ala127Thr, Arg128Ala, Gly131Lys, Gly132Thr, Met134Leu, Arg135Ser, Cys150Ser, Asn157Gly, Ser159Glu, truncated after Gly182.

16. The AGT mutant according to claim 1 with modifications Lys32Ile, Leu33Phe, Cys62Ala, Lys125Ala, Ala127Thr, Arg128Ala, Cys150Gly, Ser151Gly, Ser152Asp, Ala154Asp, Asn157Gly, Asn157Gly, Ser159Glu, truncated after Gly182 and optionally further mutations selected from Gln115Ser, Gln116His; Gly131Lys, Gly132Thr, Met134Leu, Arg135Ser; and deletion of Leu34.

17. The AGT mutant according to claim 1 with modifications Lys32Ile, Leu33Phe, Cys62Ala, Lys125Ala, Ala127Thr, Arg128Ala, Cys150Val, Ser152Arg, Gly153Asp, Ala154Asp, Asn157Gly, Ser159Glu, truncated after Gly182 and optionally further mutations selected from Gln115Ser, Gln116His; Gly131Lys, Gly132Thr, Met134Leu, Arg135Ser; and deletion of Leu34.

18. The AGT mutant according to claim 1 with modifications Lys32Ile, Leu33Phe, Cys62Ala, Lys125Ala, Ala127Thr, Arg128Ala, Cys150Asn, Ser151Ile, Ser152Asn, Ala154Thr, Asn157Gly, Ser159Glu, truncated after Gly182 and optionally further mutations selected from Gln115Ser, Gln116His; Gly131Lys, Gly132Thr, Met134Leu, Arg135Ser; and deletion of Leu34.

19. The AGT mutant according to claim 1 with modifications Lys32Ile, Leu33Phe, Cys62Ala, Lys125Ala, Ala127Thr, Arg128Ala, Cys150Ser, Ala154Thr, Asn157Gly, Ser159Glu, truncated after Gly182 and optionally further mutations selected from Gln115Ser, Gln116His; Gly131Lys, Gly132Thr, Met134Leu, Arg135Ser; and deletion of Leu34.

20. The AGT mutant according to claim 1 with modifications Cys62Ala, Lys125Ala, Ala127Thr, Arg128Ala, Cys150Val, Ser152Arg, Gly153Asp, Ala154Asp, Asn157Gly, Ser159Glu, truncated after Gly182 and optionally further mutations selected from Gln115Ser, Gln116His; Gly131Lys, Gly132Thr, Met134Leu, Arg135Ser; and deletion of Leu34.

21. The AGT mutant according to claim 1 with modifications Cys62Ala, Lys125Ala, Ala127Thr, Arg128Ala, Cys150Gly, Ser151Gly, Ser152Asp, Ala154Asp, Asn157Gly, Ser159Glu, truncated after Gly182 and optionally further mutations selected from Gln115Ser, Gln116His; Gly131Lys, Gly132Thr, Met134Leu, Arg135Ser; and deletion of Leu34.

22. The AGT mutant according to claim 1 with modifications Cys62Ala, Lys125Ala, Ala127Thr, Arg128Ala, Cys150Glu, Ser151Gly, Ser152Glu, Ala154Arg, Asn157Gly, Ser159Glu, truncated after Gly182 and optionally further mutations selected from Gln115Ser, Gln116His; Gly131Lys, Gly132Thr, Met134Leu, Arg135Ser; and deletion of Leu34.

23. A method for detecting and/or manipulating a protein of interest wherein
the protein of interest is incorporated into a fusion protein with an AGT mutant according to claim 1 the AGT fusion protein is contacted with particular AGT substrates carrying a label, and the AGT fusion protein is detected and optionally further manipulated using the label in a system
designed for recognising and/or handling the label.

24. The method according to claim 23 wherein an AGT fusion protein mixture containing the AGT fusion protein of the protein of interest and the AGT mutant and a further AGT fusion protein is contacted with a particular substrate, for which either the AGT mutant or the further AGT is selective, the mixture is treated with a further substrate, and the AGT fusion protein of the protein of interest and the AGT mutant is detected and optionally further manipulated using the label in a system designed for recognising and/or handling the label.

25. The method according to claim 24 wherein the further substrate is added to the AGT fusion protein mixture after complete reaction of the mixture with the particular substrate.

26. The method according to claim 24 wherein the further substrate is added to the AGT fusion protein mixture together with the particular substrate.

27. The method according to claim 26 wherein, in the system designed for recognising and/or handling the label, the label of the particular substrate interacts with the label of the further substrate.

28. The method according to claim 27 wherein the label of the particular substrate and the label of the further substrate are compounds of a fluorescence resonance energy transfer pair (FRET) or one fluorophore and one quencher for a proximity assay.

29. An AGT fusion protein comprising an AGT mutant according to claim 1 and a protein of interest.

30. The AGT mutant according to claim 1 wherein, when compared to the wild type human AGT, two or more advantageous properties selected from
  (a) reduced DNA interaction;
or
  (b) localisation of the expressed protein in eukaryotic cells that is no longer restricted to the nucleus;
  (c) improved expression yield as soluble protein and improved stability in various hosts;
  (d) improved stability under oxidising conditions;
  (e) improved stability within cells after reaction with a substrate;
  (f) improved stability outside cells before and after reaction with a substrate;
  (g) improved in vitro solubility;
  (h) improved reactivity against O6-alkylguanine substrates;
  (i) reduced reactivity against DNA-based substrates; and
  (j) reduced reactivity against N9-substituted O6-alkylguanine substrates, are observed.

31. The AGT mutant according to claim 30 wherein the advantageous properties are
  (c) improved expression yield as soluble protein and improved stability in various hosts and
  (h) improved reactivity against O6-alkylguanine substrates;
or
  (c) improved expression yield as soluble protein and improved stability in various hosts,
  (d) improved stability under oxidising conditions,
  (g) improved in vitro solubility, and
  (h) improved reactivity against O6-alkylguanine substrates;
or
  (c) improved expression yield as soluble protein and improved stability in various hosts,
  (d) improved stability under oxidising conditions,
  (f) improved stability outside cells before and after reaction with a substrate,
  (g) improved in vitro solubility, and
  (h) improved reactivity against O6-alkylguanine substrates;
or
  (a) reduced DNA interaction,
  (b) localisation of the expressed protein in eukaryotic cells that is no longer restricted to the nucleus,
  (c) improved expression yield as soluble protein and improved stability in various hosts,
  (h) improved reactivity against O6-alkylguanine substrates, and
  (i) reduced reactivity against DNA-based substrates;
or
  (a) reduced DNA interaction,
  (b) localisation of the expressed protein in eukaryotic cells that is no longer restricted to the nucleus,
  (c) improved expression yield as soluble protein and improved stability in various hosts,
  (e) improved stability within cells after reaction with a substrate,
  (h) improved reactivity against O6-alkylguanine substrates, and
  (i) reduced reactivity against DNA-based substrates;
or
  (a) reduced DNA interaction,
  (b) localisation of the expressed protein in eukaryotic cells that is no longer restricted to the nucleus,
  (c) improved expression yield as soluble protein and improved stability in various hosts,
  (h) improved reactivity against O6-alkylguanine substrates,
  (i) reduced reactivity against DNA-based substrates, and
  (j) reduced reactivity against N9-substituted O6-alkylguanine substrates;
or
  (a) reduced DNA interaction,
  (b) localisation of the expressed protein in eukaryotic cells that is no longer restricted to the nucleus,
  (c) improved expression yield as soluble protein and improved stability in various hosts,
  (e) improved stability within cells after reaction with a substrate,
  (h) improved reactivity against O6-alkylguanine substrates,
  (i) reduced reactivity against DNA-based substrates, and
  (j) reduced reactivity against N9-substituted O6-alkylguanine substrates.

32. The AGT mutant according to claim 30 wherein the advantageous properties are
  (c') improved expression yield as soluble protein and improved stability in *E. coli* and (h) improved reactivity against O6-alkylguanine substrates;
or
  (c') improved expression yield as soluble protein and improved stability in *E. coli*,
  (d) improved stability under oxidising conditions,
  (g) improved in vitro solubility, and
  (h) improved reactivity against O6-alkylguanine substrates;
or
  (c') improved expression yield as soluble protein and improved stability in *E. coli*,
  (d) improved stability under oxidising conditions,
  (f') improved stability outside cells after reaction with a substrate,
  (g) improved in vitro solubility, and
  (h) improved reactivity against O6-alkylguanine substrates;
or
  (a) reduced DNA interaction,
  (b) localisation of the expressed protein in eukaryotic cells that is no longer restricted to the nucleus,
  (c') improved expression yield as soluble protein and improved stability in *E. coli*,
  (h) improved reactivity against O6-alkylguanine substrates, and
  (i) reduced reactivity against DNA-based substrates;
or
  (a) reduced DNA interaction,
  (b) localisation of the expressed protein in eukaryotic cells that is no longer restricted to the nucleus,
  (c') improved expression yield as soluble protein and improved stability in *E. coli*,
  (e) improved stability within cells after reaction with a substrate, (h) improved reactivity against O6-alkylguanine substrates, and
(i) reduced reactivity against DNA-based substrates;
or
(a) reduced DNA interaction,
(b) localisation of the expressed protein in eukaryotic cells that is no longer restricted to the nucleus,
(c') improved expression yield as soluble protein and improved stability in *E. coli*,
(h) improved reactivity against O6-alkylguanine substrates,
(i) reduced reactivity against DNA-based substrates, and
(j) reduced reactivity against N9-substituted O6-alkylguanine substrates;
or
(a) reduced DNA interaction,
(b) localisation of the expressed protein in eukaryotic cells that is no longer restricted to the nucleus,
(c') improved expression yield as soluble protein and improved stability in *E. coli*,
(e) improved stability within cells after reaction with a substrate,
(h) improved reactivity against O6-alkylguanine substrates,
(i) reduced reactivity against DNA-based substrates, and
(j) reduced reactivity against N9-substituted O6-alkylguanine substrates.

33. The AGT mutant according to claim 30 wherein the advantageous properties are
(c) more than fivefold expression yield as soluble protein and improved stability in various hosts and
(h) improved reactivity against O6-alkylguanine substrates;
or
(c) more than fivefold expression yield as soluble protein and improved stability in various hosts,
(d) more than fivefold stability under oxidising conditions,
(g) more than fivefold in vitro solubility, and
(h) more than fivefold reactivity against O6-alkylguanine substrates;
or
(c) more than fivefold expression yield as soluble protein and improved stability in various hosts,
(d) more than fivefold stability under oxidising conditions,
(f) more than fourfold stability outside cells before and after reaction with a substrate,
(g) more than fivefold in vitro solubility, and
(h) improved reactivity against O6-alkylguanine substrates;
or
(a) less than 2% of DNA binding,
(b) localisation of the expressed protein in eukaryotic cells that is no longer restricted to the nucleus,
(c) more than fivefold expression yield as soluble protein and improved stability in various hosts,
(h) more than fivefold reactivity against O6-alkylguanine substrates, and
(i) less than 1% reactivity against DNA-based substrates;
or
(a) less than 2% of DNA binding,
(b) localisation of the expressed protein in eukaryotic cells that is no longer restricted to the nucleus,
(c) more than fivefold expression yield as soluble protein and improved stability in various hosts,
(e) more than threefold stability within cells after reaction with a substrate,
(h) more than fivefold reactivity against O6-alkylguanine substrates, and
(i) less than 1% reactivity against DNA-based substrates;
or
(a) less than 2% of DNA binding,
(b) localisation of the expressed protein in eukaryotic cells that is no longer restricted to the nucleus,
(c) more than fivefold expression yield as soluble protein and improved stability in various hosts,
(h) more than fivefold reactivity against O6-alkylguanine substrates,
(i) less than 1% reactivity against DNA-based substrates, and
(j) less than 2% reactivity against N9-substituted O6-alkylguanine substrates;
or
(a) less than 2% of DNA binding,
(b) localisation of the expressed protein in eukaryotic cells that is no longer restricted to the nucleus,
(c) more than fivefold expression yield as soluble protein and improved stability in various hosts,
(e) more than threefold stability within cells after reaction with a substrate,
(h) more than fivefold reactivity against O6-alkylguanine substrates,
(i) less than 1% reactivity against DNA-based substrates, and
(j) less than 2% reactivity against N9-substituted O6-alkylguanine substrates.

34. The AGT mutant according to claim 30 wherein the advantageous properties are
(c') more than fivefold expression yield as soluble protein and improved stability in *E. coli* and
(h) improved reactivity against O6-alkylguanine substrates;
or
(c') more than fivefold expression yield as soluble protein and improved stability in *E. coli*,
(d) more than fivefold stability under oxidising conditions,
(g) more than fivefold in vitro solubility, and
(h) more than fivefold reactivity against O6-alkylguanine substrates;
or
(c') more than fivefold expression yield as soluble protein and improved stability in *E. coli*,
(d) more than fivefold stability under oxidising conditions,
(f') more than fourfold stability outside cells after reaction with a substrate,
(g) more than fivefold in vitro solubility, and
(h) improved reactivity against O6-alkylguanine substrates;
or
(a) less than 2% of DNA binding,
(b) localisation of the expressed protein in eukaryotic cells that is no longer restricted to the nucleus,
(c') more than fivefold expression yield as soluble protein and improved stability in *E. coli*,
(h) more than fivefold reactivity against O6-alkylguanine substrates, and
(i) less than 1% reactivity against DNA-based substrates;
or
(a) less than 2% of DNA binding,
(b) localisation of the expressed protein in eukaryotic cells that is no longer restricted to the nucleus,
(c') more than fivefold expression yield as soluble protein and improved stability in *E. coli*, (e) more than threefold stability within cells after reaction with a substrate,
(h) more than fivefold reactivity against O6-alkylguanine substrates, and
(i) less than 1% reactivity against DNA-based substrates;

or
(a) less than 2% of DNA binding,
(b) localisation of the expressed protein in eukaryotic cells that is no longer restricted to the nucleus,
(c') more than fivefold expression yield as soluble protein and improved stability in E. coli,
(h) more than fivefold reactivity against O6-alkylguanine substrates,
(i) less than 1% reactivity against DNA-based substrates, and
(j) less than 2% reactivity against N9-substituted O6-alkylguanine substrates;

or
(a) less than 2% of DNA binding,
(b) localisation of the expressed protein in eukaryotic cells that is no longer restricted to the nucleus,
(c') more than fivefold expression yield as soluble protein and improved stability in E. coli,
(e) more than threefold stability within cells after reaction with a substrate,
(h) more than fivefold reactivity against O6-alkylguanine substrates,
(i) less than 1% reactivity against DNA-based substrates, and (0) less than 2% reactivity against N9-substituted O6-alkylguanine substrates.

35. The AGT mutant according to claim 30 wherein the advantageous properties are
(c) more than tenfold expression yield as soluble protein and improved stability in various hosts,
(d) more than tenfold stability under oxidising conditions,
(f) more than sixfold stability outside cells before and after reaction with a substrate,
(g) more than tenfold in vitro solubility, and
(h) more than tenfold reactivity against O6-alkylguanine substrates;

or
(a) no detectable DNA binding,
(b) localisation of the expressed protein in eukaryotic cells that is no longer restricted to the nucleus,
(c) more than tenfold expression yield as soluble protein and improved stability in various hosts,
(e) more than sixfold stability within cells after reaction with a substrate,
(h) more than tenfold reactivity against O6-alkylguanine substrates, and
(i) no detectable reactivity against DNA-based substrates;

or
(a) no detectable DNA binding,
(b) localisation of the expressed protein in eukaryotic cells that is no longer restricted to the nucleus,
(c) more than tenfold expression yield as soluble protein and improved stability in various hosts,
(e) more than sixfold stability within cells after reaction with a substrate,
(h) more than tenfold reactivity against O6-alkylguanine substrates,
(i) no detectable reactivity against DNA-based substrates, and
(j) no detectable reactivity against N9-substituted O6-alkylguanine substrates;

or
(a) reduced DNA interaction,
(b) localisation of the expressed protein in eukaryotic cells that is no longer restricted to the nucleus,
(c) more than tenfold expression yield as soluble protein and improved stability in various hosts,
(d) more than tenfold stability under oxidising conditions,
(e) more than sixfold stability within cells after reaction with a substrate,
(f) more than sixfold stability outside cells before and after reaction with a substrate,
(g) more than tenfold in vitro solubility,
(h) more than tenfold reactivity against O6-alkylguanine substrates, and
(i) no detectable reactivity against DNA-based substrates;

or
(a) reduced DNA interaction,
(b) localisation of the expressed protein in eukaryotic cells that is no longer restricted to the nucleus,
(c) more than tenfold expression yield as soluble protein and improved stability in various hosts,
(d) more than tenfold stability under oxidising conditions,
(e) more than sixfold stability within cells after reaction with a substrate,
(f) more than sixfold stability outside cells before and after reaction with a substrate,
(g) more than tenfold in vitro solubility,
(h) more than tenfold reactivity against O6-alkylguanine substrates,
(i) no detectable reactivity against DNA-based substrates, and
(j) no detectable reactivity against N9-substituted O6-alkylguanine substrates.

36. The AGT mutant according to claim 30 wherein the advantageous properties are
(c') more than tenfold expression yield as soluble protein and improved stability in E. coli,
(d) more than tenfold stability under oxidising conditions,
(f') more than sixfold stability outside cells after reaction with a substrate,
(g) more than tenfold in vitro solubility, and
(h) more than tenfold reactivity against O6-alkylguanine substrates;

or
(a) no detectable DNA binding,
(b) localisation of the expressed protein in eukaryotic cells that is no longer restricted to the nucleus,
(c') more than tenfold expression yield as soluble protein and improved stability in E. coli,
(e) more than sixfold stability within cells after reaction with a substrate,
(h) more than tenfold reactivity against O6-alkylguanine substrates, and
(i) no detectable reactivity against DNA-based substrates;

or
(a) no detectable DNA binding,
(b) localisation of the expressed protein in eukaryotic cells that is no longer restricted to the nucleus,
(c') more than tenfold expression yield as soluble protein and improved stability in E. coli,
(e) more than sixfold stability within cells after reaction with a substrate,
(h) more than tenfold reactivity against O6-alkylguanine substrates, (i) no detectable reactivity against DNA-based substrates, and
(j) no detectable reactivity against N9-substituted O6-alkylguanine substrates;

or (a) reduced DNA interaction,
(b) localisation of the expressed protein in eukaryotic cells that is no longer restricted to the nucleus,
(c') more than tenfold expression yield as soluble protein and improved stability in *E. coli*,
(d) more than tenfold stability under oxidising conditions,
(e) more than sixfold stability within cells after reaction with a substrate,
(f) more than sixfold stability outside cells after reaction with a substrate,
(g) more than tenfold in vitro solubility,
(h) more than tenfold reactivity against O6-alkylguanine substrates, and
(i) no detectable reactivity against DNA-based substrates;

or (a) reduced DNA interaction,
(b) localisation of the expressed protein in eukaryotic cells that is no longer restricted to the nucleus,
(c') more than tenfold expression yield as soluble protein and improved stability in *E. coli*,
(d) more than tenfold stability under oxidising conditions,
(e) more than sixfold stability within cells after reaction with a substrate,
(f) more than sixfold stability outside cells after reaction with a substrate,
(g) more than tenfold in vitro solubility,
(h) more than tenfold reactivity against O6-alkylguanine substrates,
(i) no detectable reactivity against DNA-based substrates, and
(j) no detectable reactivity against N9-substituted O6-alkylguanine substrates.

* * * * *

UNITED STATES PATENT AND TRADEMARK OFFICE
CERTIFICATE OF CORRECTION

| | |
|---|---|
| PATENT NO. | : 7,888,090 B2 |
| APPLICATION NO. | : 10/591159 |
| DATED | : February 15, 2011 |
| INVENTOR(S) | : Jan Barnikow et al. |

It is certified that error appears in the above-identified patent and that said Letters Patent is hereby corrected as shown below:

At column 3, line number 18, change "□" to --µ--

At column 3, line number 19, change "□" to --µ--

At column 3, line number 21, change "□" to --µ--

At column 3, line number 30, change "□" to --µ--

At column 3, line number 31, change "□" to --µ--

At column 3, line number 33, change "□" to --µ--

At column 3, line number 35, change "□" to --µ--

At column 4, line number 49, change "Gin115" to --Gln11--

At column 4, line number 45, change "□" to --µ--

At column 17, line number 60, change "□l" to --µl-- and change "□M" to --µM--

At column 17, line number 61, change "□" to --µ--

At column 18, line number 9, change "□" to --µ--

At column 19, line number 28, change "□" to --µ--

At column 19, line number 48, change "□" to --µ-- twice

At column 20, line number 67, change "□" to --µ--

At column 21, line number 29, change "□" to --µ--

At column 21, line number 35, change "□" to --µ--

At column 21, line number 37, change "□" to --µ--

At column 21, line number 42, change "□" to --µ--

At column 21, line number 63, change "□M" to --µM-- and "□" to --β--

At column 21, line number 64, change "□" to --µ--

At column 22, line number 1, change "□" to --β--

At column 22, line number 5, change "□" to --µ--

Signed and Sealed this
Twenty-second Day of November, 2011

David J. Kappos
*Director of the United States Patent and Trademark Office*

At column 22, line number 7, change "□" to --µ--

At column 22, line number 27, change "□" to --µ-- twice

At column 22, line number 30, change "□" to --µ--

At column 22, line number 38, change "□" to --µ--

At column 22, line number 7, change "□" to --µ--

SEQUENCE LISTING

<160> NUMBER OF SEQ ID NOS: 48

<210> SEQ ID NO 1
<211> LENGTH: 624
<212> TYPE: DNA
<213> ORGANISM: Homo sapiens

<400> SEQUENCE: 1

```
atggacaagg attgtgaaat gaaacgcacc acactggaca gcccctttggg gaagctggag      60 ctgtctggtt gtgagcaggg tctgcacgaa ataaagctcc tgggcaaggg gacgtctgca     120
gctgatgccg tggaggtccc agcccccgct gcggttctcg gaggtccgga gccctgatg      180 cagtgcacag cctggctgaa tgcctatttc caccagcccg aggctatcga agagttcccc     240
gtgccggcac ttcaccatcc cgtttttccag caagagtcgt tcaccagaca ggtgttatgg     300
aagctgctga aggttgtgaa attcggagaa gtgatttctt accagcaatt agcagccctg     360
gcaggcaacc ccaaagccgc gcgagcagtg ggaggagcaa tgagaggcaa tcctgtcccc     420
atcctcatcc cgtgccacag agtggtctgc agcagcggag ccgtgggcaa ctactccgga     480
ggactggccg tgaaggaatg gcttctggcc catgaaggcc accggtttggg gaagccaggc     540 ttgggaggga gctcaggtct ggcaggggcc tggctcaagg gagcgggagc tacctcgggc     600 tcccccgcctg ctggccgaaa ctga                                            624
```

<210> SEQ ID NO 2
<211> LENGTH: 22
<212> TYPE: DNA
<213> ORGANISM: Artificial Sequence
<220> FEATURE:

```
<223> OTHER INFORMATION: Substrate oligonucleotide containing
      O6-Benzylguanine at position 14
<220> FEATURE:
<221> NAME/KEY: misc_feature
<222> LOCATION: (14)..(14)
<223> OTHER INFORMATION: n is O6-benzylguanine

<400> SEQUENCE: 2
gtggtgggca gctnaggcgt gg                                              22

<210> SEQ ID NO 3
<211> LENGTH: 33
<212> TYPE: DNA
<213> ORGANISM: Artificial Sequence
<220> FEATURE:
<223> OTHER INFORMATION: Sense primer for cloning AGT into pGEX

<400> SEQUENCE: 3
cgaaatggat ccatggacaa ggattgtgaa atg                                  33

<210> SEQ ID NO 4
<211> LENGTH: 43
<212> TYPE: DNA
<213> ORGANISM: Artificial Sequence
<220> FEATURE:
<223> OTHER INFORMATION: Antisense primer for cloning AGT into pGEX

<400> SEQUENCE: 4
gcctttgaat ccgtctttg tagtcgtttc ggccagcagg cgg                        43

<210> SEQ ID NO 5
<211> LENGTH: 31
<212> TYPE: DNA
<213> ORGANISM: Artificial Sequence
<220> FEATURE:
<223> OTHER INFORMATION: Sense primer for mutating K125A, T127A,
      R128A

<400> SEQUENCE: 5
gcaaccccgc agccacggca gcagtgggag g                                    31

<210> SEQ ID NO 6
<211> LENGTH: 31
<212> TYPE: DNA
<213> ORGANISM: Artificial Sequence
<220> FEATURE:
<223> OTHER INFORMATION: Antisense primer for mutating K125A, T127A,
      R128A

<400> SEQUENCE: 6
cctcccactg ctgccgtggc tgcggggttg c                                    31

<210> SEQ ID NO 7
<211> LENGTH: 49
<212> TYPE: DNA
<213> ORGANISM: Artificial Sequence
<220> FEATURE:
<223> OTHER INFORMATION: Sense primer for cloning into eukaryotic
      pNUC vector

<400> SEQUENCE: 7
gatcgagcta gcgctaccgg tcgccaccat ggacaaggat tgtgaaatg                 49

<210> SEQ ID NO 8
<211> LENGTH: 31
<212> TYPE: DNA
<213> ORGANISM: Artificial Sequence
```

```
<220> FEATURE:
<223> OTHER INFORMATION: Antisense primer for cloning into
      eukaryotic pNUC vector

<400> SEQUENCE: 8
gctagggatc ctacgtttcg gccagcaggc g                              31

<210> SEQ ID NO 9
<211> LENGTH: 35
<212> TYPE: DNA
<213> ORGANISM: Artificial Sequence
<220> FEATURE:
<223> OTHER INFORMATION: Sense primer for mutating Cys 62 to Ala

<400> SEQUENCE: 9
gagcccctga tgcaggctac agcctggctg aatgc                          35

<210> SEQ ID NO 10
<211> LENGTH: 35
<212> TYPE: DNA
<213> ORGANISM: Artificial Sequence
<220> FEATURE:
<223> OTHER INFORMATION: Antisense primer for mutating Cys 62 to Ala

<400> SEQUENCE: 10
gcattcagcc aggctgtagc ctgcatcagg ggctc                          35

<210> SEQ ID NO 11
<211> LENGTH: 60
<212> TYPE: DNA
<213> ORGANISM: Artificial Sequence
<220> FEATURE:
<223> OTHER INFORMATION: Sense primer for cloning of AGT mutants
      into phage-display vector

<400> SEQUENCE: 11
ctactcgcgg cccagccggc catggcggac tacaaagaca tggacaagga ttgtgaaatg    60

<210> SEQ ID NO 12
<211> LENGTH: 40
<212> TYPE: DNA
<213> ORGANISM: Artificial Sequence
<220> FEATURE:
<223> OTHER INFORMATION: Antisense primer for cloning of AGT mutants
      into phage-display vector

<400> SEQUENCE: 12
ggaattcggc ccccgaggcc gcgtttcggc cagcaggcgg                     40

<210> SEQ ID NO 13
<211> LENGTH: 42
<212> TYPE: DNA
<213> ORGANISM: Artificial Sequence
<220> FEATURE:
<223> OTHER INFORMATION: Antisense primer for cloning AGT truncated
      after 182 into pGEX

<400> SEQUENCE: 13
gcctttgaat tccgtctttg tagtctccca agcctggctt cc                  42

<210> SEQ ID NO 14
<211> LENGTH: 50
<212> TYPE: DNA
<213> ORGANISM: Artificial Sequence
<220> FEATURE:
<223> OTHER INFORMATION: Sense primer for randomisation of codons
      131-135
```

```
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 14
cccaaagccg cgcgagcagt gnnknnkgca nnknnkggca atcctgtccc          50

<210> SEQ ID NO 15
<211> LENGTH: 26
<212> TYPE: DNA
<213> ORGANISM: Artificial Sequence
<220> FEATURE:
<223> OTHER INFORMATION: Antisense primer for randomisation of
      codons 131-135

<400> SEQUENCE: 15
tgctcgcgcg gctttggggt tgcctg                                   26

<210> SEQ ID NO 16
<211> LENGTH: 41
<212> TYPE: DNA
<213> ORGANISM: Artificial Sequence
<220> FEATURE:
<223> OTHER INFORMATION: Sense primer for randomisation of codons
      115-116
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 16
ggagaagtga tttcttacnn bnnbttagca gccctggcag g                  41

<210> SEQ ID NO 17
<211> LENGTH: 27
<212> TYPE: DNA
<213> ORGANISM: Artificial Sequence
<220> FEATURE:
<223> OTHER INFORMATION: Antisense primer for randomisation of
      codons 115-116

<400> SEQUENCE: 17
gtaagaaatc acttctccga atttcac                                  27

<210> SEQ ID NO 18
<211> LENGTH: 41
<212> TYPE: DNA
<213> ORGANISM: Artificial Sequence
<220> FEATURE:
<223> OTHER INFORMATION: Sense primer for randomisation of codons
      150-152
<220> FEATURE:
<221> NAME/KEY: misc_feature
<222> LOCATION: (19)..(20)
```

<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t

<400> SEQUENCE: 18
ccgtgccaca gagtggtcnn bnnbnnbgga gccgtgggcg g          41

<210> SEQ ID NO 19
<211> LENGTH: 18
<212> TYPE: DNA
<213> ORGANISM: Artificial Sequence
<220> FEATURE:
<223> OTHER INFORMATION: Antisense primer for randomisation of
      codons 150-152

<400> SEQUENCE: 19
gaccactctg tggcacgg          18

<210> SEQ ID NO 20
<211> LENGTH: 35
<212> TYPE: DNA
<213> ORGANISM: Artificial Sequence
<220> FEATURE:
<223> OTHER INFORMATION: Sense primer for mutating G131K, G132T,
      M134L, R135S

<400> SEQUENCE: 20
gcagccacgg cagcagtgaa gacggcactg agtgg          35

<210> SEQ ID NO 21
<211> LENGTH: 40
<212> TYPE: DNA
<213> ORGANISM: Artificial Sequence
<220> FEATURE:
<223> OTHER INFORMATION: Antisense primer for mutating G131K, G132T,
      M134L, R135S

<400> SEQUENCE: 21
ggatagggac aggattgcca ctcagtgccg tcttcactgc          40

<210> SEQ ID NO 22
<211> LENGTH: 41
<212> TYPE: DNA
<213> ORGANISM: Artificial Sequence
<220> FEATURE:
<223> OTHER INFORMATION: Sense primer for mutating Q115S, Q116H

<400> SEQUENCE: 22
gtgaaattcg gagaagtgat ttcttactct cacttagcag c          41

<210> SEQ ID NO 23
<211> LENGTH: 35
<212> TYPE: DNA
<213> ORGANISM: Artificial Sequence
<220> FEATURE:
<223> OTHER INFORMATION: Antisense primer for mutating Q115S, Q116H

<400> SEQUENCE: 23
cctgccaggg ctgctaagtg agagtaagaa atcac          35

<210> SEQ ID NO 24

<210> SEQ ID NO 24
<211> LENGTH: 33
<212> TYPE: DNA
<213> ORGANISM: Artificial Sequence
<220> FEATURE:
<223> OTHER INFORMATION: Sense primer for mutating C150N, S151I, S152N

<400> SEQUENCE: 24
cgtgccacag agtggtcaat atcaatggag ccg                    33

<210> SEQ ID NO 25
<211> LENGTH: 32
<212> TYPE: DNA
<213> ORGANISM: Artificial Sequence
<220> FEATURE:
<223> OTHER INFORMATION: Antisense primer for mutating C150N, S151I, S152N

<400> SEQUENCE: 25
cgtaaccgcc cacggctcca ttgatattga cc                     32

<210> SEQ ID NO 26
<211> LENGTH: 32
<212> TYPE: DNA
<213> ORGANISM: Artificial sequence
<220> FEATURE:
<223> OTHER INFORMATION: Primer for cloning mutant AGT in pET15b

<400> SEQUENCE: 26
gtcgcatatg gacaaggatt gtgaaatgaa ac                     32

<210> SEQ ID NO 27
<211> LENGTH: 34
<212> TYPE: DNA
<213> ORGANISM: Artificial sequence
<220> FEATURE:
<223> OTHER INFORMATION: Primer for cloning mutant AGT in pET15b

<400> SEQUENCE: 27
gattacggga tccttatccc aagcctggct tccc                   34

<210> SEQ ID NO 28
<211> LENGTH: 45
<212> TYPE: DNA
<213> ORGANISM: Artificial Sequence
<220> FEATURE:
<223> OTHER INFORMATION: Antisense primer for cloning truncated AGT in pAK 100

<400> SEQUENCE: 28
gcaatggaat tcggcccccg aggccgctcc caagcctggc ttccc       45

<210> SEQ ID NO 29
<211> LENGTH: 81
<212> TYPE: DNA
<213> ORGANISM: Artificial Sequence
<220> FEATURE:
<223> OTHER INFORMATION: Sense primer for introducing 12xHis, SbfI and AscI sites

<400> SEQUENCE: 29
ttatccatgg cacatcatca tcatcatcat catcatcatc atcatcatcc tgcaggtata    60
ggcgcgccta aaagcttctt a                                 81

<210> SEQ ID NO 30
<211> LENGTH: 81

-continued

<210> SEQ ID NO 30
<211> LENGTH: 81
<212> TYPE: DNA
<213> ORGANISM: Artificial Sequence
<220> FEATURE:
<223> OTHER INFORMATION: Antisense primer for introducing 12xHis,
    SbfI and AscI sites

<400> SEQUENCE: 30
taagaagctt ttaggcgcgc ctatacctgc aggatgatga tgatgatgat gatgatgatg    60
atgatgatgt gccatggata a                                              81

<210> SEQ ID NO 31
<211> LENGTH: 59
<212> TYPE: DNA
<213> ORGANISM: Artificial Sequence
<220> FEATURE:
<223> OTHER INFORMATION: Sense primer for cloning mutant AGT in
    pBAD-HisA

<400> SEQUENCE: 31
ggcctgcagg tgaaaacctg tacttccagg gtatggacaa ggattgtgaa atgaaacgc    59

<210> SEQ ID NO 32
<211> LENGTH: 45
<212> TYPE: DNA
<213> ORGANISM: Artificial Sequence
<220> FEATURE:
<223> OTHER INFORMATION: Antisense primer for cloning mutant AGT in
    pBAD-HisA

<400> SEQUENCE: 32
aaaaggcgcg ccggatcctt atcccaagcc tggcttcccc aaccg                    45

<210> SEQ ID NO 33
<211> LENGTH: 47
<212> TYPE: DNA
<213> ORGANISM: Artificial Sequence
<220> FEATURE:
<223> OTHER INFORMATION: Antisense primer for cloning wt AGT in
    pBAD-HisA

<400> SEQUENCE: 33
aacggcgcgc cggatcctta gtttcggcca gcaggcgggg agcccga                  47

<210> SEQ ID NO 34
<211> LENGTH: 49
<212> TYPE: DNA
<213> ORGANISM: Artificial Sequence
<220> FEATURE:
<223> OTHER INFORMATION: Sense primer for cloning AGTM in pEGFP-Nuc

<400> SEQUENCE: 34
gatcgagcta gcgctaccgg tcgccaccat ggacaaggat tgtgaaatg                49

<210> SEQ ID NO 35
<211> LENGTH: 32
<212> TYPE: DNA
<213> ORGANISM: Artificial Sequence
<220> FEATURE:
<223> OTHER INFORMATION: Antisense primer for cloning AGT G160W in
    pEGFP-Nuc

<400> SEQUENCE: 35
ccaggcagat ctgtttcggc cagcaggcgg gg                                  32

<210> SEQ ID NO 36
<211> LENGTH: 48

```
<210> SEQ ID NO 36
<211> LENGTH: 48
<212> TYPE: DNA
<213> ORGANISM: Artificial Sequence
<220> FEATURE:
<223> OTHER INFORMATION: Antisense primer for cloning AGTM in pEGFP-
      Nuc

<400> SEQUENCE: 36
ccaggcagat cttcccaagc ctggcttccc caaccggtgg ccttcatg                  48

<210> SEQ ID NO 37
<211> LENGTH: 33
<212> TYPE: DNA
<213> ORGANISM: Artificial Sequence
<220> FEATURE:
<223> OTHER INFORMATION: Sense primer for cloning beta-Gal in pEGFP-
      Nuc

<400> SEQUENCE: 37
catcgtctag attatttttg acaccagacc aac                                  33

<210> SEQ ID NO 38
<211> LENGTH: 42
<212> TYPE: DNA
<213> ORGANISM: Artificial Sequence
<220> FEATURE:
<223> OTHER INFORMATION: Antisense primer for cloning beta-Gal in
      pEGPF-Nuc

<400> SEQUENCE: 38
gatcgagatc tgggtccgga atgactaaat ctcattcaga ag                        42

<210> SEQ ID NO 39
<211> LENGTH: 25
<212> TYPE: DNA
<213> ORGANISM: Artificial Sequence
<220> FEATURE:
<223> OTHER INFORMATION: Sense primer for mutation G160W

<400> SEQUENCE: 39
caactactcc tggggactgg ccgtg                                           25

<210> SEQ ID NO 40
<211> LENGTH: 25
<212> TYPE: DNA
<213> ORGANISM: Artificial Sequence
<220> FEATURE:
<223> OTHER INFORMATION: Antisense primer for mutation G160W

<400> SEQUENCE: 40
ccagtcccca ggagtagttg cccac                                           25

<210> SEQ ID NO 41
<211> LENGTH: 39
<212> TYPE: DNA
<213> ORGANISM: Artificial Sequence
<220> FEATURE:
<223> OTHER INFORMATION: Primer for error prone PCR of pAK100 insert,
      c at position 1 modified with biotin
<220> FEATURE:
<221> NAME/KEY: misc_feature
<222> LOCATION: (1)..(1)
<223> OTHER INFORMATION: n is c modified with biotin

<400> SEQUENCE: 41
ngatccttag acctgaacgc aggtttcccg actggaaag                            39

<210> SEQ ID NO 42
```

```
<211> LENGTH: 39
<212> TYPE: DNA
<213> ORGANISM: Artificial Sequence
<220> FEATURE:
<223> OTHER INFORMATION: Antisense primer for error prone PCR of
      pAK100 insert

<400> SEQUENCE: 42
gcgtcagggt tacaagttca tggtttacca gcgccaaag                            39

<210> SEQ ID NO 43
<211> LENGTH: 19
<212> TYPE: DNA
<213> ORGANISM: Artificial Sequence
<220> FEATURE:
<223> OTHER INFORMATION: Sense primer for amplification of
      errorprone-PCR product

<400> SEQUENCE: 43
cgatccttag acctgaacg                                                  19

<210> SEQ ID NO 44
<211> LENGTH: 19
<212> TYPE: DNA
<213> ORGANISM: Artificial Sequence
<220> FEATURE:
<223> OTHER INFORMATION: Antisense primer for amplification of
      errorprone-PCR product

<400> SEQUENCE: 44
gcgtcagggt tacaagttc                                                  19

<210> SEQ ID NO 45
<211> LENGTH: 48
<212> TYPE: DNA
<213> ORGANISM: Artificial Sequence
<220> FEATURE:
<223> OTHER INFORMATION: Sense primer for saturation mutagenesis AGTM
      150-154
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 45
cgtgccacag agtggtcnnk nnknnknnkn nkgtgggcgg ttacgagg                  48

<210> SEQ ID NO 46
<211> LENGTH: 48
<212> TYPE: DNA
<213> ORGANISM: Artificial Sequence
<220> FEATURE:
<223> OTHER INFORMATION: Antisense primer for saturation mutagenesis
      AGTM 150-154
<220> FEATURE:
```

```
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 46
cctcgtaacc gcccacmnnm nnmnnmnnmn ngaccactct gtggcacg         48

<210> SEQ ID NO 47
<211> LENGTH: 48
<212> TYPE: DNA
<213> ORGANISM: Artificial Sequence
<220> FEATURE:
<223> OTHER INFORMATION: Sense primer for saturation mutagenesis AGTM
      31-35
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t

<400> SEQUENCE: 47
gcagggtctg cacgaannkn nknnknnknn kaaggggacg tctgcagc         48

<210> SEQ ID NO 48
<211> LENGTH: 48
<212> TYPE: DNA
<213> ORGANISM: Artificial Sequence
<220> FEATURE:
<223> OTHER INFORMATION: Antisense primer for saturation mutagenesis
      AGTM 31-35
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
```

-continued

```
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t

<400> SEQUENCE: 48
gctgcagacg tccccttmnn mnnmnnmnnm nnttcgtgca gaccctgc            48
```